US009096849B2

(12) United States Patent
Archer et al.

(10) Patent No.: US 9,096,849 B2
(45) Date of Patent: Aug. 4, 2015

(54) SOLID PHASE FOR CAPTURE OF NUCLEIC ACIDS

(75) Inventors: Marie J. Archer, Alexandria, VA (US); Baochuan Lin, Bethesda, MD (US); David A Stenger, Herndon, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 714 days.

(21) Appl. No.: 11/751,096

(22) Filed: May 21, 2007

(65) Prior Publication Data

US 2008/0293594 A1    Nov. 27, 2008

(51) Int. Cl.
*C12Q 1/68*  (2006.01)
*C12N 15/10* (2006.01)
*C40B 30/04* (2006.01)
*C40B 40/08* (2006.01)
*C40B 50/18* (2006.01)

(52) U.S. Cl.
CPC ........ *C12N 15/1006* (2013.01); *C12N 15/1013* (2013.01); *C12Q 1/68* (2013.01); *C40B 30/04* (2013.01); *C40B 40/08* (2013.01); *C40B 50/18* (2013.01); *C07B 2200/11* (2013.01)

(58) Field of Classification Search
CPC ....................................................... C12Q 1/68
USPC ................... 435/6.1, 6.11, 6.12, 91.2, 283.1; 422/50, 420, 68.1, 69, 129, 131, 138, 422/600
See application file for complete search history.

(56) References Cited

U.S. PATENT DOCUMENTS

| | | | |
|---|---|---|---|
| 5,834,020 A | 11/1998 | Margerum et al. | |
| 5,876,937 A | 3/1999 | Sillekens | |
| 5,994,066 A * | 11/1999 | Bergeron et al. | 435/6 |
| 6,238,866 B1 | 5/2001 | Yeh et al. | |
| 7,501,251 B2 * | 3/2009 | Koster et al. | 435/6 |
| 2002/0012940 A1 | 1/2002 | Lockhart et al. | |
| 2003/0077595 A1 | 4/2003 | Van Ness et al. | |
| 2003/0235822 A1 | 12/2003 | Lokhov et al. | |
| 2004/0023248 A1* | 2/2004 | O'Malley | 435/6 |
| 2005/0100893 A1 | 5/2005 | Gunderson et al. | |
| 2005/0186601 A1 | 8/2005 | Szasz | |
| 2005/0214767 A1 | 9/2005 | Trevisiol et al. | |
| 2007/0248969 A1 | 10/2007 | Sampath et al. | |
| 2009/0298054 A1 | 12/2009 | Lesche et al. | |

FOREIGN PATENT DOCUMENTS

WO          02/33125        4/2002

OTHER PUBLICATIONS

Koblizkova et al., BioTechniques, vol. 25, No. 1, pp. 32-38 (1998).*
Waner et al., Biophysical Journal, vol. 87, No. 4, pp. 2701-2713 (2004).*
Muir et al., Journal of Clinical Microbiology, vol. 31, No. 1, pp. 31-38 (1993).*
PCT Search Report and Written Opinion.
Archer et al., "Magnetic bead-based solid phase for selective extraction of genomic DNA" *Anal. Biochem.*, 2006, 355, 285-297.
Beaucage, "Strategies in the Preparation of DNA Oligonucleotide Arrays for Diagnostic Applications" *Current Medicinal Chemistry*, 2001,8, 1213-1244.
Beier et al., "Versatile derivatisation of solid support media for covalent bonding on DNA-microchips" *Nucleic Acids Res.*, 1999, 27(9), 1970-1977.
Benters et al "DNA microarrays with PAMAM dendritic linker systems" *Nucleic Acids Res.*, 2002, 30(2), e10.
Biotraces, Inc., "Toward MPD enabled direct detection of DNA" website.
Caminade et al., "Nanomaterials Based on Phosphorus Dendrimers" *Accounts of Chemical Research*, 2004, 37(6), 341-348.
Day et al., "Multithiolated dendrimers as linkers for DNA immobilization on gold surfaces" abstract, The 81st ACS Colloid & Surface Science Symposium.
Fan et al., "Dynamic DNA Hybridization on a Chip Using Paramagnetic Beads" *Anal. Chem.*, 1999, 71, 4851-4859.
Hawkins et al., "DNA purification and isolation using a solid-phase" *Nucleic Acids Res.*, 1994, 22(21), 4543-4544.
Hong et al., "Self-Assembly of a Dendron through Multiple Ionic Interaction to Give Mesospacing between Reactive Amine Groups on the Surface" *Langmuir* 2003, 19, 2357-2365.
Hong et al., "Nanoscale-controlled spacing provides DNA microarrays with the SNP discrimination efficiency in solution phase" *Langmuir*, 2005, 21, 4257-4261.
Launey et al., "Synthesis of bowl-shaped dendrimers from generation 1 to generation 8" *J. Organometallic Chem.*, 1997, 529, 51-58.
Le Berre et al., "Dendrimeric coating of glass slides for sensitive DNA microarrays analysis" *Nucleic Acids Res.*, 31 (2003) e88.
Lund et al., "Assessment of methods for covalent binding of nucleic acids to magnetic beads, Dynabeads™, and the characteristics of the bound nucleic acids in hybridization reactions" *Nucleic Acids Res.*, 16 (1988) 10861-10880.
Mangiapan et al., "Sequence Capture-PCR Improves Detection of Mycobacterial DNA in Clinical Specimens" *J. Clin. Microbiol.*, 1996, 34(5), 1209-1215.

(Continued)

*Primary Examiner* — Ardin Marschel
(74) *Attorney, Agent, or Firm* — US Naval Research Laboratory; Joseph T. Grunkemeyer

(57) ABSTRACT

A method of: providing a solid surface having a dendrimer molecule bound thereto and a single-stranded probe nucleic acid immobilized to the dendrimer; contacting the solid surface with a sample suspected or known to contain a double-stranded complimentary target nucleic acid; denaturing the target nucleic acids at thermal conditions and in a salt concentration sufficient to denature the target nucleic acids to produce denatured nucleic acids; and cooling the sample to allow hybridization of the denatured nucleic acids to the probe nucleic acids. An article having: one or more paramagnetic microbeads; a dendrimer molecule bound to the beads; and a probe nucleic acid immobilized to the dendrimer.

16 Claims, 8 Drawing Sheets

(56) References Cited

OTHER PUBLICATIONS

Millar et al., "Solid-phase hybridization capture of low-abundance target DNA sequences: application to the polymerase chain reaction detection of *Mycobacterium paratuberculosis* and *Mycobacterium avium* subsp. *Silvaticum*" *Anal. Biochem.*, 226 (1995) 325-330.

Odeberg et al., "Dynamic analysis of heterogeneous hepatitis C virus populations by direct solid-phase sequencing" *J. Clin. Microbiol.*, 33 (1995) 1870-1874.

Olsvik et al., "Magnetic separation techniques in diagnostic microbiology", *Clin. Microbiol. Rev.*, 7 (1994) 43-54.

Sjöroos et al., "Solid-phase PCR with hybridization and time resolved fluorometry for detection of HLA-B27", *Clin. Chem.*, 47 (2001) 498-504.

Trévisol et al., "Dendrislides, dendrichips: a simple chemical functionalization of glass slides with phosphorus dendrimers as an effective means for the preparation of biochips", *New J. Chem.*, 27 (2003) 1713-1719.

Zammatteo et al., "Comparison between microwell and bead supports for the detection of human cytomegalovirus amplicons for sandwich hybridization", *Anal. Biochem.*, 253 (1997) 180-189.

Day et al. "Immobilization of polynucleotides on magnetic particles. Factors influencing hybridization efficiency" *Biochem. J.* (1991) 278, 735-740.

Ross et al., "Discrimination of Single-Nucleotide Polymorphisms in Human DNA Using Peptide Nucleic Acid Probes Detected by MALDI-TOF Mass Spectrometry" *Anal. Chem.* 1997, 69, 4197-4202.

Yeung et al., "Manipulation and extraction of genomic DNA from cell lysate by functionalized magnetic particles for lab on a chip applications" Biosensors and Bioelectronics 21 (2006) 989-997.

Chandler et al., "Automated nucleic acid isolation and purification from soil extracts using renewable affinity microcolumns in a sequential injection system" Talanta 49 (1999) 969-983.

Yoza et al., "DNA extraction using bacterial magnetic particles modified with hyperbranched polyamidoamine dendrimer" Journal of Biotechnology 101 (2003) 219-228.

Office Action in U.S. Appl. No. 12/264, 462 (Sep. 18, 2009).

U.S. Appl. No. 12/264,462, filed Nov. 4, 2008.

Denz et al., "The benefits of 28S rRNA for standardization of reverse transcription-polymerase chain reaction for studying gene expression" Anal. Biochem., 341, 382-384 (2005).

Groebe et al., "Thermal Stability of RNA Hairpins Containing a Four-Membered Loop and a Bulge Nucleotide" Biochem., 28, 742-747 (1989).

Office Action in U.S. Appl. No. 121264, 462 (Mar. 12, 2010).
Office Action in U.S. Appl. No. 12/264,462 (Sep. 20, 2010).
Office Action in U.S. Appl. No. 12/264,462 (Aug. 9, 2011).
Office action in U.S. Appl. No. 12/264,462 (Dec. 13, 2011).
Advisory action in U.S. Appl. No. 12/264,462 (Apr. 18, 2012).

* cited by examiner

SOLID PHASE FOR CAPTURE OF NUCLEIC ACIDS

The attached sequence listing, filed electronically, is incorporated herein by reference.

FIELD OF THE INVENTION

The invention is generally related to the capture of nucleic acid targets.

DESCRIPTION OF RELATED ART

The selective separation of nucleic acids (DNA and RNA) from complex mixtures is required in many applications in which the diagnosis of a disease state or the presence of foreign organisms relies on the identification of a specific genetic signature. Since the sequence of interest is sometimes present in a lower abundance than the commonly occurring ones (e.g. background), it is necessary to minimize the background and/or isolate it completely in order to enhance the sensitivity and the yield of the downstream processes. This background minimization can be performed using enzymatic degradation of undesired DNA (which leaves RNA intact) or multiple rounds of subtractive hybridization coupled with a solid phase. Selective enzymatic digestion is useful when the nucleic acid of interest is RNA, but it cannot be used in any application requiring the study of DNA and RNA sequences simultaneously. In subtractive hybridization, the target DNA or RNA is first hybridized in solution with a capture probe or a "driver sequence" which has been prepared to contain a linking moiety at the end. The complex, capture probe-target is then hybridized to a solid phase with surface functionalities that will bind to the linking moiety of the capture probe. These two steps, solution phase capture and solid phase binding, are performed separately under different media (salt concentration) and temperature conditions. This separation can be performed, for example, with commercially available streptavidin-coated magnetic beads. FIG. 1 shows a schematic representation of the selective subtraction of genomic DNA using a streptavidin-coated solid phase.

The subtraction of the genomic DNA is performed in a two-step process that involves melting of the double stranded genomic DNA (dsDNA) at high temperatures (up to 95° C.) in a high salt media (3-5 M NaCl) followed by annealing to a biotinylated capture DNA probe. The biotinylated complex (capture DNA probe/background genomic DNA) must then be annealed onto streptavidin-coated magnetic beads and the supernatant containing the DNA of interest is removed after the magnetic isolation of the beads. This process requires multiple manual manipulations which makes it liable to contamination or loss of template. The capture of genomic DNA using biotinylated capture probes linked to the streptavidin-coated beads in a single step has been attempted with unsatisfactory results. (Sheibani et al., "Subtraction with 3' modified oligonucleotides eliminates amplification artifacts in DNA libraries enriched for microsatelites" *BioTechniques*, 25 (1998) 32-38. All referenced publications and patent documents are incorporated herein by reference.) This is mainly due to the degradation of the streptavidin-biotin bond which has been observed at temperatures as low as 87° C. with millimolar concentrations of sodium chloride (NaCl), and in certain detergents, such as sodium dodecyl sulfate (SDS), that are essential components of the hybridization buffer making it impossible to use for the subtraction of background genomic DNA in a single step under the required high temperature and salt conditions. The lack of robustness in the biotin-streptavidin link also limits the possibility of releasing the captured targets from the solid phase using heat denaturation. In addition, it is almost impossible to reuse the solid phase (Waner et al., "Thermal and sodium dodecylsulfate induced transitions of streptavidin" *Biophys. J*, 87 (2004) 2701-2713). An additional concern with the use of the two-step approach is the possibility that endogenous biotin present in tissue samples might interfere with the hybridization between the biotinylated capture probes and the targets.

There has been a significant advance in the development of covalent attachment strategies of DNA probes onto different types of solid supports (glass, silicon, plastics, and magnetic microbeads etc.) and the variables affecting the immobilized probes (Zanmatteo et al., "Comparison between different strategies of covalent attachment of DNA to glass surfaces to build DNA microarrays" *Anal. Biochem.*, 280 (2000) 143-150; Levicky et al., "Physicochemical perspectives on DNA microarray and biosensor technologies" *Trends Biotechnol.*, 23 (2005) 143-149; Dugas et al., "Immobilization of single-stranded DNA fragments to solid surfaces and their repeatable specific hybridization: covalent bonding or adsorption?" *Sens. Actuators, B*, 101 (2004) 112-121; Southern et al., "Molecular interaction on microarrays" *Nature Genet.*, 21 (1999) 5-9; Shchepinov et al., "Steric factors influencing hybridization of nucleic acids to oligonucleotide arrays" *Nucleic Acids Res.*, 25 (1997) 1155-1161; Beucage, "Strategies in the preparation of DNA oligonucleotide arrays for diagnostic applications" *Current Medicinal Chemistry*, 8 (2001) 1213-1244; Lund et al., "Assessment of methods for covalent binding of nucleic acids to magnetic beads, Dynabeads™, and the characteristics of the bound nucleic acids in hybridization reactions" *Nucleic Acids Res.*, 16 (1988) 10861-10880; Zammatteo et al., "Comparison between microwell and bead supports for the detection of human Cytomegalovirus amplicons for sandwich hybridization" *Anal. Biochem.*, 253 (1997) 180-189), there is no documented evidence of the robustness of any of these strategies under high salt and temperature conditions. This is mainly due to the fact that the final use of the prepared substrates is not intended for selective subtraction of genomic DNA but rather for microarrays and DNA chips in which the hybridization is performed under mild temperature and salt conditions. Furthermore, there is no documented approach on the immobilization of probes longer than 300 bp on any type of solid phase which are required to capture long genomic targets.

Le Berre and coworkers (Le Berre et al., "Dendrimeric coating of glass slides for sensitive DNA microarrays analysis" *Nucleic Acids Res.*, 31 (2003) e88; Trévisol et al., "Dendrislides, dendrichips: a simple chemical functionalization of glass slides with phosphorous dendrimers as an effective means for the preparation of biochips" *New J. Chem.*, 27 (2003), 1713-1719) reported the use of a novel surface chemistry to prepare microarrays with covalently bound DNA sequences using a "dendrimeric linker system." These dendrimer linkers are "bowl" shaped structures in which the generation is proportional to the size and the number of aldehyde branches available for covalent linking. For instance, a generation 0 dendrimer will be 15 Å in size with 6 aldehyde branches while a generation 4 dendrimer will be 75 Å in size with 96 aldehyde branches (FIG. 2). These two characteristics provide spacing between the surface and the capture probe as well as between the probes hence, reducing steric hindrance which is a critical factor in microarray DNA hybridization. Furthermore, since the dendrimerization of surfaces results in an electrically neutral surface, non-specific adsorption of capture probes during their immobilization is minimal. By using dendrimeric linkers, this group demonstrated an enhancement in the hybridization efficiency in comparison with the commercially available slides for microarrays. The same group reported the regeneration of the microarrays up to ten times by heating at 95° C. in a low salt containing buffer. Subsequent use of these regenerated microarrays demonstrated significantly better results than those using commercially available glass slides. Evidently, dendrimeric linkers could provide many of the desirable characteristics in a selective solid phase but there are no reports on the use, or proposed use, of these macromolecules for the development of a solid phase intended to selectively subtract genomic DNA.

A process to covalently bond the phosphorous dendrimers on glass slides is contained in Trevisiol et al., US Patent Application Publication 2005/0214767, which pertains to the preparation of glass substrates for the immobilization of oligonucleotides and other biomolecules to fabricate microarrays.

SUMMARY OF THE INVENTION

The invention comprises a method comprising: providing a solid surface having a dendrimer molecule bound thereto and a single-stranded probe nucleic acid immobilized to the dendrimer; contacting the solid surface with a sample suspected or known to contain a double-stranded complimentary target nucleic acid; denaturing the target nucleic acids at thermal conditions and in a salt concentration sufficient to denature the target nucleic acids to produce denatured nucleic acids; and cooling the sample to allow hybridization of the denatured nucleic acids to the probe nucleic acids.

The invention further comprises an article comprising: one or more paramagnetic microbeads; a dendrimer molecule bound to the beads; and a probe nucleic acid immobilized to the dendrimer.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
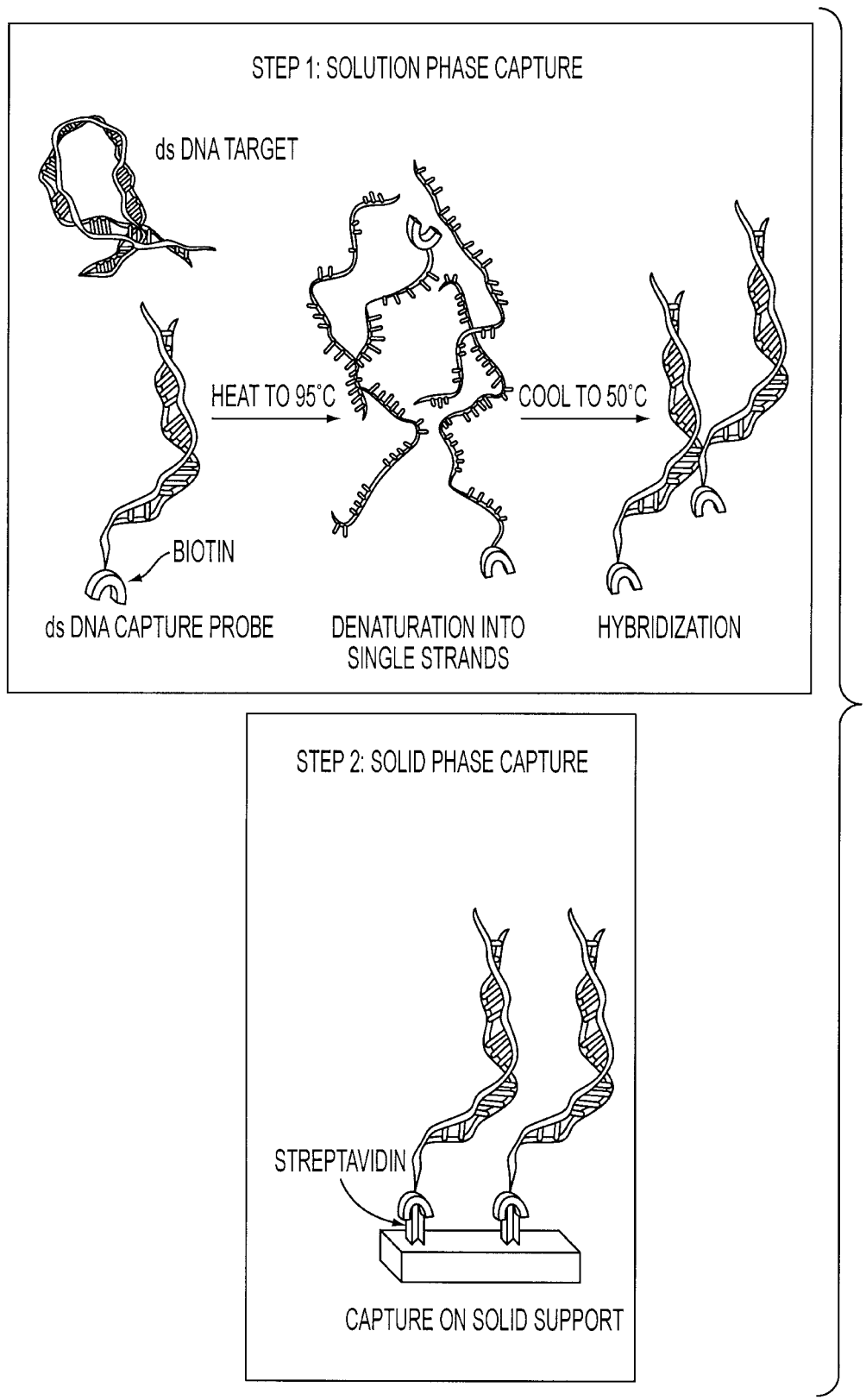
FIG. 1 shows a schematic representation of a two-step selective capture of genomic DNA using a commercially available streptavidin-coated solid phase (e.g. magnetic beads).

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The disclosed process relates in general to the use of a thermally stable solid phase for the selective capture of genomic DNA in a single step. More particularly, the process pertains to the use of functionalized solid supports, for example, silicon structures, glass beads of various sizes or paramagnetic microparticles, to selectively capture a desired target and release it from the solid phase for further analysis. Yet even more particularly, the process concerns specific procedures for the fabrication of such thermally stable selective solid phase using paramagnetic microbeads and the protocols used for the immobilization of the capture probes and the hybridization with the DNA targets. The process may enable the subtraction of genomic DNA to be performed in a single step in which the DNA is first denatured at high temperature (90-100° C.) and salt (3-5 M NaCl) conditions and then captured by the probes immobilized on the solid phase. The capturing may be by cooling without changing the salt concentration. The solid phase can be thermally regenerated either for a new subtraction or to recover the captured DNA.

This technology has potential applications in any research area requiring the study or identification of genomic nucleic acid sequences present at low abundance in complex matrices (numerous types of nucleic acids) that have to be selectively isolated from interference or background materials prior to any downstream process. The technology also reduced the complexity of the prior two-step process into one single step, which is amenable for automation processes.

Selective isolation of nucleic acids was commonly performed using two-step process: (i) hybridization of capture probe and target using high temperature in the presence of high salt media and (ii) hybridization of the probe-target complex onto the solid phase. The disclosed process may provide an alternative, one-step process for selectively capturing nucleic acids and addressing the challenges of selectively separate specific DNA molecules (via complementary hybridization) in a single step. Disclosed is a general platform for the fabrication of selective solid phase that can be used for subtractive hybridization or sequence capture applications using phosphorus dendrimers as linkers in a selective solid phase for capture of genomic DNA. The solid support material can be, but is not limited to, glass, structured silicon, or magnetic microparticles. The branched structure of the dendrimers also provides additional spacing between the surface of the solid support and the probe DNA, which can reduce steric effects and increase the capture efficiency. Aside from providing a high loading capacity, the covalent link between the probe DNA and the solid support is thermally stable at high salt concentrations, which enables the single step process of capturing targeted nucleic acids.

The thermally stable selective solid phase to perform a selective capture of genomic DNA in a single step may provide an alternative to the currently used methods with three main potential advantages: (1) The possibility to perform selective capture of genomic DNA in a single step (rather than in two or more steps) hence, reducing the risk of contamination and loss of template. The single step process is also amenable to the automation process if desired. (2) Availability of a "custom tailored platform" to immobilize capture probes as required by a specific application. (3) Reduction of costs associated with the fabrication given the reusability of the solid phase.

Figure 2:
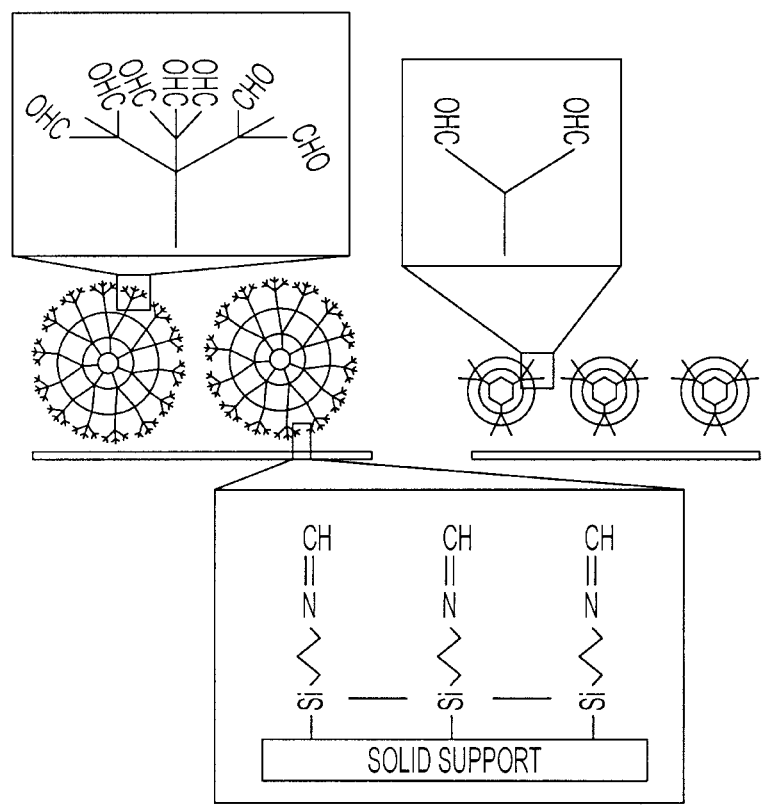
FIG. 2 shows a schematic representation of a generation 0 (G0) and a generation 4 (G4) dendrimer. A stable amine is formed between the primary amine on the substrate and the aldehyde groups of the dendrimer

The specificity of the dendrimer magnetic bead-based solid phase toward human genomic DNA may be demonstrated in two ways: (i) by the recovery of adenovirus serotype 4 DNA spiked into the human DNA targets and (ii) by the release of the captured targets followed by specific amplification of the GADPH human gene. The process for producing a thermally stable solid phase for the selective capture of genomic DNA in a single step is carried out using a substrate with a primary amine and then functionalized with a phosphorous dendrimer. A schematic of the surface functionalization is shown in FIG. 2.

The substrate material can be, but is not limited to, structured silicon, solid glass microbeads, silica beads, planar silicon wafer, and paramagnetic microbeads. Disclosed is a particular process for preparing the microparticles for the covalent immobilization of phosphorous dendrimers. The silicon and glass solid supports can be prepared by the methods described by US Patent Application Publication 2005/0214767 but their use for the intended purpose of the present invention in not known to be documented or suggested in the exiting literature. The process to functionalize magnetic microparticles with a phosphorous dendrimer is not known to be patented or documented, nor are the specific protocols for the immobilization of the capture probes on the prepared magnetic beads, the subtraction or regeneration processes and the composition of the various solutions used.

Figure 3:
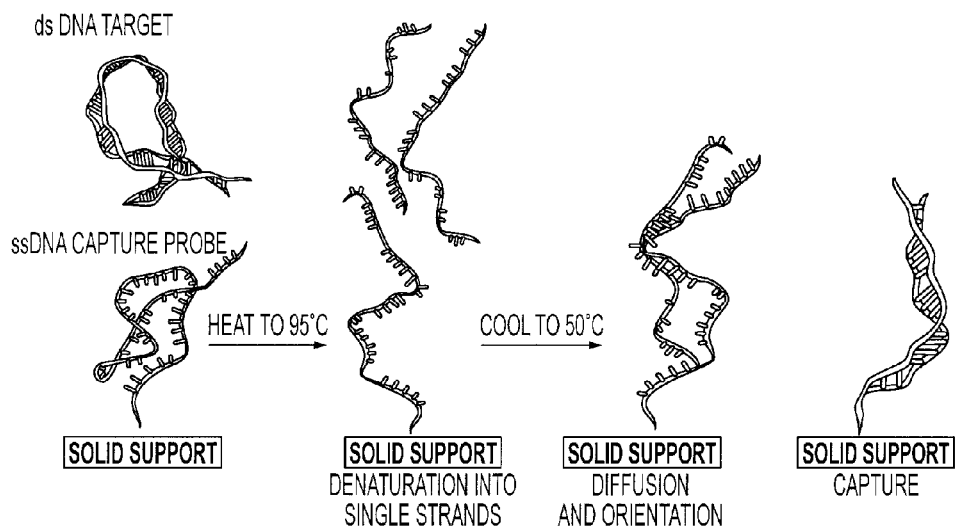
FIG. 3 shows a schematic representation of a single step selective capture of genomic DNA on a solid phase such as the one proposed in the present disclosure. The denaturing and capture steps are performed sequentially in a single vial.

FIG. 3 shows a schematic representation of the steps involved in the selective capture of genomic DNA in a single step. In comparison with the two-step protocol, the solid phase is present in the same vial as the target and is exposed to the denaturing step at high temperature and salt conditions. There is no known prior documented approach to perform this selective capture of genomic DNA in a single step under the required high temperature and salt conditions.

The selectivity of the solid phase is conferred by immobilizing probes onto the functionalized solid supports. This is performed by exposing the solid Support to a solution containing amino modified double stranded DNA capture probes with a length between 200 and 800 bp. A covalent bond is produced between the amino terminal of the DNA capture probe and the aldehyde reactive functions of the dendrimer. Suitable probes include, but are not limited to, single-stranded DNA, single-stranded human DNA, and single-stranded pathogen DNA. The probes are single-stranded when attached to the dendrimer, but may have been derived from double-stranded sources.

The "bowl-shaped" dendrimers differ in size (15 and 75 Å) and in number of branches (6 and 96) available for covalent coupling with amines. The aldehyde groups (—CHO) on the periphery of the dendrimer are electrically neutral, reducing the electrostatic interactions with the DNA capture probes and facilitating the covalent attachment through the aminated end. Also, the use of phosphorus dendrimers as the linker system provides the high loading capacity, reduced steric hindrance, and thermal stability required for the fabrication of a selective solid phase. In the following, the term G4 or G0 SiO2 section refers to a section of silicon oxide wafer (4×7 mm) functionalized with G4 or G0 phosphorus dendrimer. Likewise, the term G4 or G0 magnetic beads refers to magnetic beads functionalized with a G4 or G0 phosphorus dendrimer. The structure of a suitable dendrimer is shown below. The value n is a positive integer. For G0, the structure is $N_3P_3(O$—$C_6H_4$—$CHO)_6$. $N_3P_3$ is hexavalent cyclotriphosphazene. Each X is independently selected from —CHO and —$CH_2$—NH—. Each —$CH_2$—NH— group is directly or indirectly bound to the solid surface or the probe nucleic acid. There is at least one —CH2—NH— group directly or indirectly bound to the solid surface and at least one —$CH_2$—NH— group directly or indirectly bound to the probe nucleic acid. The repeating unit in parentheses indicates that phosphorous atom on the right is bound to two repeat units. The dendrimer may be made as disclosed in Launay et al., "Synthesis of bowl-shaped dendrimers from generation 1 to generation 8" *J. Organometallic Chem.*, 529 (1997) 51-58. In short, six hydroxybenzaldehyde groups are grafted onto a cyclotriphosphazene core to make G0. The second step consists of the condensation of 6 equivalents of dichlorophosphorhydrazide with the aldehyde functionalities. The repetition of these two steps, i.e. reaction with the sodium salt of hydroxybenzaldehyde and condensation with the dichlorophosphorhydrazide, ending with the hydroxybenzaldehyde step, produces successive generations of the dendrimer structure.

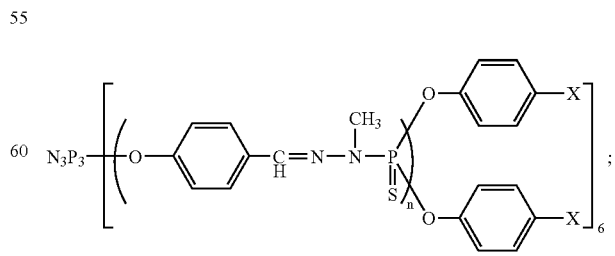

Several additional steps may be performed. The solid surface may be separated from the sample. The remaining nucleic acids in the sample after this separation may be analyzed to identify the organism of the nucleic acids. A polymerase chain reaction may be performed on the remaining nucleic acids. The hybridized nucleic acids may be removed from the solid surface after separation from the sample and a PCR performed on them.

After the immobilization period the excess probe solution is removed and the solid phase is treated with a suitable blocking/reducing solution which avoids non-specific adsorption of nucleic acids during the subtraction and stabilizes the bond between the nucleic acid and the dendrimer. In order for the DNA capture probes to hybridize with the target, they have to exist as single strands on the solid phase. The final step includes the conversion of theses double stranded DNA capture probes into single stranded ones capable of hybridizing with a target as represented in FIG. 3.

In one embodiment, the sample contains human nucleic acids or DNA and is suspected of containing pathogen nucleic acids. This would be the case with a clinical sample taken from a human patient. The probes may be complimentary to the human DNA in order to remove it and leave behind only pathogen nucleic acids for analysis and identification. Alternatively, the probes may be complementary to the pathogen nucleic acids to separate them from the human DNA, so that they can be removed from the probes and analyzed in the absence of human DNA.

The disclosed technology may have the ability to be a "universal platform" for the fabrication of solid phases which enables the user to "custom tailor" the solid phase depending on the application by selecting the solid support material (e.g. glass, silicon, magnetic microbeads) and the capture probe(s). The disclosed technology may be advantageous in those applications requiring the isolation of genomic nucleic acids in which denaturation (conversion from double stranded to single stranded DNA) and the subsequent capture by a specific probe is performed at high temperature in the presence of a high salt buffer. An additional potential advantage is the lack of any components that would inhibit down stream processes such as the polymerase chain reaction (PCR) which enables its use for solid phase synthesis and amplification. Furthermore, the performance (capture efficiency) can be tuned by changing the shape and geometry of the solid phase (e.g. magnetic microbeads, structured silicon of various geometries) and the size of the dendrimeric linker.

Having described the invention, the following examples are given to illustrate specific applications of the invention. These specific examples are not intended to limit the scope of the invention described in this application.

Example 1 general materials and methods—All chemicals used for cleaning and activation of the substrates were purchased from Sigma-Aldrich (St. Louis, Mo, USA). 3-Aminopropyltriethoxysilane (APTES) was stored in a dessicator and flushed with nitrogen after each use. Anhydrous tetrahydrofuran was used for the synthesis of the G0 phosphorus dendrimer as described by Launay et al., "Synthesis of bowl-shaped dendrimers from generation 1 to generation 8" J. Organometallic Chem., 529 (1997) 51-58, and characterized by solution phase UV spectroscopy. The G4 phosphorus dendrimer was purchased from Sigma-Aldrich and used as received. The water used for the cleaning and activation of the substrates was Milli-Q filtered deionized to 18 $\Omega$-cm resistivity. Unlabeled and labeled (Cy3) oligonucleotides were synthesized by Operon Biotechnologies (Huntsville, Al, USA). The sequences used were as follows: probe 1 (5'-NH2 ACT GCA AAT ACT ACC TTG GCT CATT-3' (SEQ ID NO 1)), target 1 (5'-AAT GAG CCA AGG TAG TAT TTG-3' (SEQ ID NO 2)), and sequence 2 (noncomplementary) (5'-AAC GGT TAG CAA TCG CCT GAC CTG CGG CGT CAT CCT TCG CGC TGT TAA TAC GCA AGC CAG AAG ACA GACG Cy-3' (SEQ ID NO 3)). The water used for the preparation of oligonucleotide stock solutions, immobilization, hybridization, and washing buffers was nuclease free, 0.2 μm filtered obtained from Ambion (Austin, Tx, USA). Stock solutions of 10% SDS and 20×SSC (3 M NaCl and 0.3 M sodium citrate) were purchased from Ambion and used as received.

Example 2

Solid support fabrication and characterization—P-type monocrystalline silicon wafers 100 with 10,000 Å thermal oxide were purchased from Iosonics (Vancouver, Wash., USA) and cleaved in 4×7-cm sections (hereafter referred to as SiO$_2$ sections). Fused silica slides (1×1 inch) were obtained from Dell Optics (Fairhaven, N.J., USA). The substrates (SiO$_2$ sections and fused silica slides) were cleaned by immersing them in a 1:1 (v/v) solution of hydrochloric acid and methanol for 12 h at room temperature. They were then rinsed with water and immersed in concentrated sulfuric acid for 24 h at room temperature. Finally, the substrates were rinsed once more until the pH of the wash media was neutral, immersed in boiling water for 30 min, and dried with nitrogen.

Silanization was performed as described by Trévisol et al., *New J. Chem.*, 27 (2003) 1713-1719. Briefly, the substrates were immersed in a 10% (v/v) solution of APTES and 95% ethanol for 12 h. Glacial acetic acid (10 μL) was added to catalyze the reaction. After silanization, the substrates were rinsed three times with 95% ethanol, rinsed three times with water, and cured in a dry oven at 120° C. for 3 h.

The dry substrates were immersed in a 1.3-M aqueous solution of potassium hydroxide for 7 min, rinsed with water, and dried at 80° C. in an oven. They were then immersed in a 1% (w/v) solution of dendrimer (G0 or G4) in dichloromethane at room temperature and incubated with gentle stirring for at least 12 h. After immobilization, they were rinsed three times each with dichloroniethane, 95% ethanol, and absolute ethanol and then were dried with nitrogen and stored in air-tight containers at room temperature inside a dessicator until used.

Superparamagnetic beads (2-3 μm) with primary amine functionalities (NH$_2$) were purchased from Chemagen (Baesweiler, Germany). Aliquots of 500 μg of beads were washed five times with 1 mL of water prior to use. It is necessary to perform a solvent exchange prior to the dendrimer immobilization because dichloromethane is poorly soluble in water. This was done using ethanol as the transition solvent between water and dichloromethane. After the last water wash, the beads were resuspended in 1 mL of absolute ethanol and incubated for 8 h with shaking at 90 rpm (ethanol was refreshed every 2 h). The beads were then resuspended in 1 mL of dichloromethane and incubated with shaking for 18 h (the solvent was refreshed every 4 h). The beads were transferred to fresh tubes after incubation and resuspended in 1 ml of a 1% (w/v) solution of dendrimer (G0 or G4) in dichloromethane, followed by incubation with shaking at 90 rpm for at least 12 h. After the immobilization, the beads were washed three times with 1 mL of dichloromethane, 95% ethanol, and absolute ethanol. Finally, the functionalized beads were resuspended in 200 μL of ethanol and realiquoted in two 0.5-mL polypropylene tubes. The ethanol supernatant was removed, and the beads were soft-baked at 60° C. in a dry block heater for 15 mill and stored at room temperature.

Solid phase UV spectroscopy of the functionalized fused silica slides with G0 or G4 dendrimer was performed using a Cary 2400 (UV-VIS-NIR) spectrophotometer (MRTL, Boulder, Colo., USA). The spectra were taken immediately after the dendrimer immobilization and 1 month later to address any detrimental effect on the functionalized substrates stored at room temperature.

Example 3

Selective solid phase fabrication—COT human DNA (Roche Applied Science, Indianapolis, Ind., USA) was selected as template for the capture probe because it poses high affinity to Alu and L1 repetitive sequences present in human DNA. Amino-modified capture probes were synthesized using primers that were manufactured with a 5' amino modifier and 6 carbon spacer (Operon Biotechnologies). Amplification was carried out using either TaKaRa Ex Taq HS (Takara Bio, Madison, Wis., USA) or Platinum Taq DNA polymerase (Invitrogen, Carlsbad, Calif., USA). For 800-bp capture probes, polymerase chain reactions (PCRs) were performed in a 50-μL volume containing 1×Ex Taq buffer, 3 mM $MgCl_2$, 200 μM each of the deoxyribonucleoside triphosphates (dNTPs), 2 μM primer D (Wang et al., "Microarray-based detection and genotyping of viral pathogens" *Proc. Natl. Acad. Sci. USA,* 99 (2002) 15687-15692), 3 U TaKaRa Ex Taq HS, and 1 μg of COT human DNA. The amplification reaction was carried out in a Peltier Thermal Cycler-PTC240 DNA Engine Tetrad 2 (MJ Research, Reno, Nev., USA) with preliminary denaturation at 95° C. for 3 min, followed by 40 cycles of 95° C. for 30 s, 58° C. for 30 s, and 72° C. for 60 s. For 100- to 300-bp capture probes, PCRs were performed in a 50-μL volume containing 20 mM Tris-HCl (pH 8.4), 50 mM KCl, 2 mM $MgCl_2$, 200 μM dNTPs, 2 μM each of primers, 2 U Platinum Taq DNA polymerase, and 1 ng of DNA templates. The amplification reaction was carried out in a Peltier Thermal Cycler-PTC240 DNA Engine Tetrad 2 with preliminary denaturation at 95° C. for 3 min, followed by 40 cycles of: 95° C. for 30 s, 50° C. for 30 s, and 72° C. for 60 s. For 600-bp capture probes amplification, the method reported by Bohlander et al., "A method for the rapid sequence-independent amplification of micro-dissected chromosomal material" *Genomics,* 13 (1992) 1322-1324 was adapted using Sequenase DNA polymerase (version 2.0, USB, Cleveland, Ohio, USA). The reaction was carried out in a 15-μL volume containing 40 mM Tris-HCl (pH 7.5), 20 mM $MgCl_2$, 40 mM NaCl, 20 μM primer D, 67 μM dNTPs, 4 U Sequenase DNA polymerase (version 2.0), and 2 μg of COT human DNA. The amplification reaction was carried out in a Peltier Thermal Cycler-PTC240 DNA Engine Tetrad 2 with preliminary denaturation at 95° C. for 2 min, followed by incubation at 10° C. for 5 min and 37° C. for 20 min. dNTPs and Sequenase DNA polymerase were added after the denaturation step. All of the amplified products were purified by incubating with 5 μL of ExoSAP-IT (USB) at 37° C. for 30 min and passing through ProbeQuant G-50 Micro Columns (Amersham Biosciences, Piscataway, N.J., USA) to remove unused primers and nucleotides, and they were stored at 4° C. until used. The amplified products were electrophoresed on 1.2% TAE agarose gels and visualized by ethidium bromide staining. The concentration of the PCR products was determined with a NanoDrop ND-1000 fluorospectrometer (NanoDrop Technologies, Wilmington, Del., USA). When required, incorporation of biotin on COT human DNA was performed with terminal transferase (TdT, New England Biolabs, Ipswich, Mass., USA) following the manufacturer's recommended protocol.

The immobilization on $SiO_2$ sections was performed by distributing 315 ng of probe 1 in 15 μL of 0.3 M sodium phosphate buffer at pH 9.0 ($Na_2HPO_4$) evenly over the surface. One side was left without capture probe to corroborate the lack of nonspecific binding during the hybridization experiments. After the immobilization period, the $SiO_2$ sections were allowed to dry at room temperature over a period of 3 h.

The magnetic beads were washed in 100 μL of 0.3 M sodium phosphate buffer at pH 9.0 and incubated for 8 h at room temperature with four additional buffer changes. The beads were transferred to a fresh 0.5-mL polypropylene tube, the wash buffer was removed, and they were incubated with 750 ng of probe (probe 1 or PCR products) in 50 μL sodium phosphate buffer for up to 8 h at room temperature. The percentage of capture probes immobilized on the beads at different periods of time was calculated as $1-(C/C_o)$, where C is the concentration of the supernatant of the beads and $C_o$ is the concentration of the diluted capture probe before addition to the magnetic beads. The measurements were performed using a Nano-Drop ND-1000 fluorospectrometer. After incubation, the supernatant with the remaining capture probe was collected and measured, and the beads were washed three more times with 50 μL of the sodium phosphate to collect any additional unbound probe. The supernatant of each wash was collected and quantified.

The reduction of the imine functions was performed using a solution of sodium borohydride (12.5 mg $NaBH_4$ in 15 ml of phosphate-buffered saline [PBS] at pH 7.0 and 5 mL of absolute ethanol) for 7-10 min at room temperature. After the reduction/blocking step, the $SiO_2$ sections and the magnetic beads were washed three times in 0.2% SDS for 1 min, washed three times with nuclease-free water, and transferred to a fresh 0.5-mL polypropylene tube.

Double-stranded PCR capture probes were denatured into single strands by immersing the magnetic beads in 150 μL of a stripping buffer (1×SCC/1% SDS) and heating to 95° C. for 10 min. The supernatant was collected in a polypropylene tube. Although only the magnetic beads were immobilized with double-stranded PCR products, the $SiO_2$ sections were also subjected to this step to ensure the stability of the solid support under the exact same conditions.

Example 4

Preparation of targets for subtractive hybridization experiments—For the subtractive hybridization experiments, 400 ng of purified human genomic DNA (Roche Applied Science) was fragmented by endonuclease digestion using McrBC (New England Biolabs) in a reaction volume of 20 μL. The fragmented DNA was concentrated using a ChargeSwitch PCR Clean-Up Kit (Invitrogen) and eluting in a 10-μL final volume. When required, incorporation of a Cy3 label to the human genomic DNA was performed by fragmentation of DNA as described above, followed by incorporation of Cy3 with TdT. The size range of the digested product was determined by gel electrophoresis on 1.2% TAE agarose gel, visualized by ethidium bromide staining, and determined to be between 500 bp and 12 kbp. For the specificity experiments, 1 ng of genomic adenovirus serotype 4 DNA was spiked into the fragmented DNA. PCR was performed to confirm the recovery of adenovirus 4 DNA.

Example 5

Figure 4:
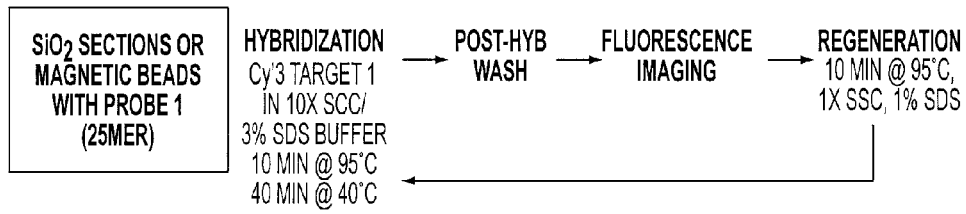
FIG. 4 shows a schematic representation of the experimental methods performed for the thermal stability experiments and the subtractive hybridization. Post-hyb, posthybridization; HGDNA, human genomic DNA.
Figure 4:
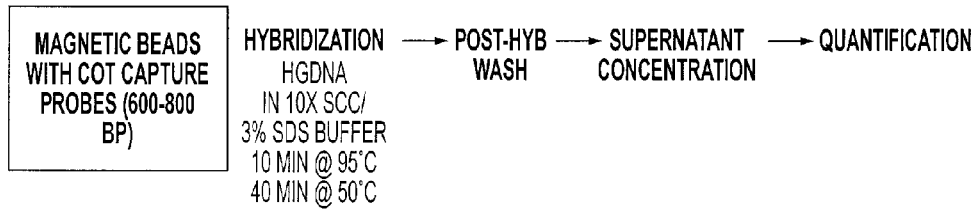

Performance characterization of the selective solid phase—All hybridization and regeneration experiments were performed in a Peltier Thermal Cycler-PTC240 DNA Engine Tetrad 2. A schematic representation of the two main sets of experiments performed in this study is presented in FIG. 4.

For the thermal stability and selectivity experiments, 500 ng of target 1 and sequence 2 (noncomplementary) was mixed with 60 µL of hybridization buffer (10×SSC/3% SDS) to ensure complete immersion of the SiO$_2$ sections. The SiO$_2$ sections were incubated for 10 min at 95° C. and then ramped down to 40° C. (0.1° C./min) and held at that temperature for 40 min. For the magnetic beads, the final volume was balanced to 50 µL and the same temperature profile was used for the experiments. Two reference samples with either target 1 or sequence 2 but no solid phases were prepared for each set of experiments and subjected to the exact same conditions.

For the subtractive hybridization experiments, 200 ng of the human genomic DNA was mixed with the hybridization buffer (10×SSC/3% SDS) to a final volume of 50 µL. The beads prepared with the COT capture probes were washed once with 50 µL of the hybridization buffer prewarmed at 70° C. before adding the prepared target. The beads were resuspended by tapping the bottom of the tube and incubated at 95° C. for 10 min to denature the double-stranded DNA fragments, and the temperature was ramped down to 50° C. (0.1° C./min) and held for 40 min to allow hybridization of the capture probe and the DNA target. Two reference samples (no beads, only the target in the hybridization buffer) were prepared for each set of subtraction experiments and subjected to the exact same conditions. The subtraction efficiency was obtained with respect to these references to account for any variations on the amount of DNA during the process. An additional set of experiments was performed as described above using the fragmented human DNA spiked with the adenovirus serotype 4 DNA to ensure the specificity of the beads.

In both sets of experiments (thermal stability and subtractive hybridization), the beads were resuspended twice by pipetting during the ramp from the melting step to the annealing step and three more times during the annealing step.

For the two-step subtractive hybridization protocol, 500 ng of biotinylated COT was mixed with 200 ng of the human genomic DNA, and the final volume was balanced to 75 µL with the hybridization buffer (10×SSC/3% SDS) and incubated as described above. Then 200 µg of streptavidin-coated beads (Bioclone, San Diego, Calif., USA) was washed twice with nuclease-free water and equilibrated with 75 µL of 2×PBS with 0.2% bovine serum albumin (BSA). The hybridized sample was mixed with the prepared streptavidin magnetic beads, and the hybridization was performed at 37° C. on a heat block for 30 min with periodic resuspension. After hybridization, the supernatant was collected into a 1.5-mL polypropylene tube, the streptavidin beads were washed once with 150 mL of 1×PBS with 0.1% BSA, and the supernatant was transferred to the collection tube. Ethanol precipitation was performed at −20° C. for 45 min by adding 1/10 volume of sodium acetate (pH 5.5), 4 µL of glycogen, and two volumes of 100% ethanol. The supernatants were centrifuged at room temperature at 16,100 g for 30 min, and the pellets were washed twice with 70% ethanol and resuspended in 20 µL of nuclease-free water.

After hybridization, the samples were washed once with 50 µL (for the magnetic beads) or 70 µL (for the SiO$_2$ sections) of the hybridization buffer, once with 100 µL of wash 1 solution (1×SSC/0.3% SDS), and washed twice with 100 µL of wash 2 solution (0.1×SSC/0.03% SDS). The supernatants were collected after each wash in a 1.5-mL polypropylene tube for concentration and quantification. A second magnetic separation of the bead supernatant was performed prior to the concentration step to eliminate any bead carryover. The reference samples were transferred to a 1.5-mL polypropylene tube, and the same wash volumes were added to maintain the same conditions as with the hybridized samples.

For the regeneration and rehybridization experiments, the hybridized SiO$_2$ sections and magnetic beads prepared with probe 1 were immersed in 150 µL of a stripping buffer (1×SCC/1% SDS) and heated to 95° C. for 5 min, and the supernatant was collected before a second wash for an additional 5 min with 150 µL of the stripping buffer pre-warmed to 95° C. The SiO$_2$ substrates and the magnetic beads were finally washed with 100 µL of 10 mM Tris-HCl (pH 8.5) and transferred to a fresh 0.5 mL polypropylene tube before rehybridization.

Fluorescence images were taken with a Nikon Eclipse E800 microscope (Nikon Instruments, Melville, N.Y., USA) interfaced with a Sony DKC-500 digital photo camera (Sony Electronics, San Jose, Calif., USA). The SiO$_2$ sections were placed on a clean microscope slide and scanned. The magnetic beads were resuspended in 3 µL of nuclease-free water, and 1 µL of the suspension was dispersed on a clean microscope slide. To avoid variations in the amount of beads used for each regeneration-hybridization cycle, the beads were recovered from the glass slide and mixed with the original aliquot. The intensity analysis was performed using the GNU Image Manipulation Program (freely distributed software available at www.gimp.org) by recording the mean value of the histogram for each image. The values were then normalized to the maximum intensity, and the percentage difference in the intensity between the high temperature cycles was plotted against the cycle number.

The release of the captured human DNA target from the beads was performed immediately after the posthybridization wash in four steps by heating at 95° C. under variable stringency conditions for 10 min each as follows: twice with 1×SCC and 1% SDS, once with nuclease-free water, and then once with 10×SSC/3% SDS. The supernatants were collected into a 1.5-mL polypropylene tube for concentration and quantification.

All supernatants from the single-step subtractive hybridization experiments (including the reference samples and the released targets) were concentrated using the CHARGESWITCH® PCR Clean-Up Kit. For this purpose, the suggested protocol for purification of PCR products was modified to reconcentrate from larger volumes (400-500 µL) with higher salt concentration and to a final elution volume of 12 µL. The quantification of the recovered targets from the single- and two-step protocols was performed using a Nano-Drop ND-1000 fluorospectrometer. The percentage of DNA hybridized to the solid support was obtained as 1−(C/C$_o$), where C is the concentration of the recovered sample and C$_o$ is the concentration of the reference.

PCR was performed on the recovered spiked targets, adenovirus serotype 4, and the released human DNA targets with the same conditions described for the selective solid phase preparation using specific primers for adenovirus serotype 4 (forward: 5'-GTT GCT AAC TAC GAT CCA GAT ATT G-3' (SEQ ID NO 4); reverse: 5'-CCT GGT AAG TGT CTG TCA ATC C-3' (SEQ ID NO 5)) and the GADPH gene (forward: 5'-GTG AAG GTC GGA GTC ACG G-3' (SEQ ID NO 6); reverse: 5'-GCC AGT GGA CTC CAC GAC GTA-3' (SEQ ID NO 7)). The amplified products were electrophoresed on 1.2% TAE agarose gels and visualized by ethidium bromide staining.

Example 6

Figure 5:
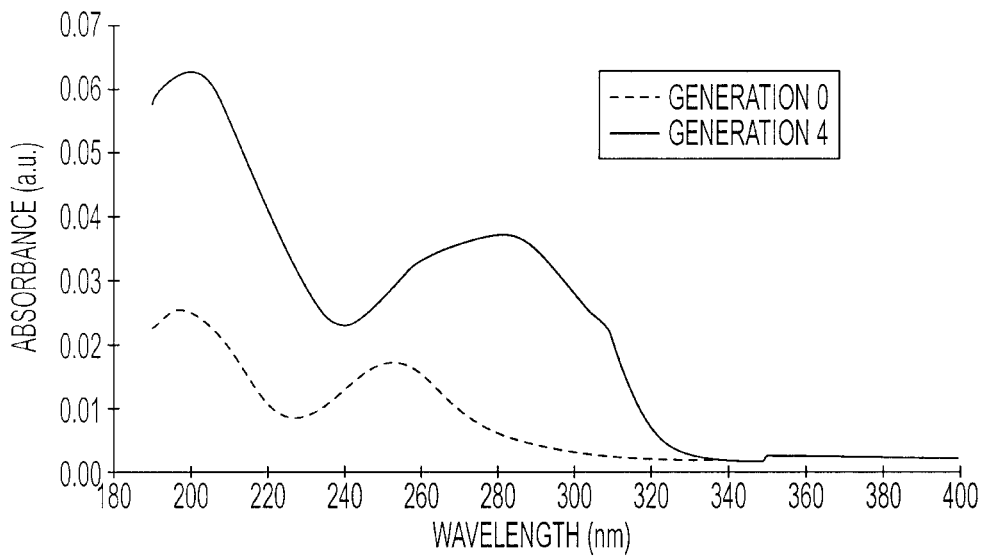
FIG. 5 shows the UV spectra of fused silica slides functionalized with a G0 dendrimer and a G4 dendrimer. The spectra were taken on freshly prepared substrates to corroborate the immobilization of the dendrimer.

Results—Solid support fabrication and characterization—
Before studying the stability and efficiency of the dendrimers attached to a solid support, it was established that the surface was being functionalized. UV spectroscopy was performed on prepared fused silica slides. FIG. 5 presents the absorbance versus wavelength for the fused silica slides functionalized with G0 and G4 dendrimers. The same peaks were observed in the solution phase UV spectra (results not shown) that indicate the attachment of the dendrimers on the surface. The extended conjugation length in the G4 dendrimer is responsible for the bathochromic (higher wavelength) and hyperchromic (higher absorbance) shifts as well as the shoulders of the second peak.

Figure 6:
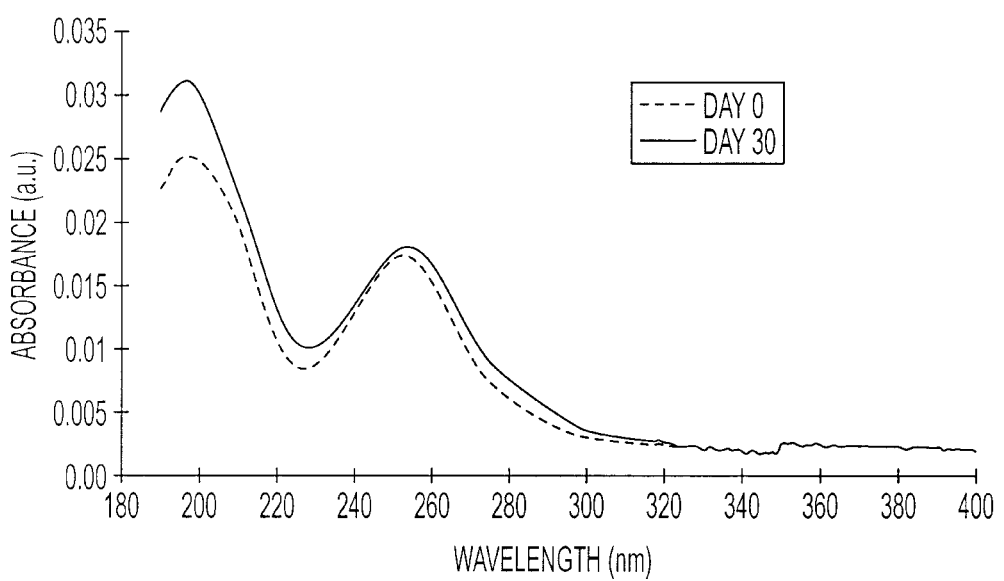
FIG. 6 shows a comparison of the UV spectra on fused silica functionalized with a G0 dendrimer immediately after immobilization (day 0) and 1 month later (day 30).
Figure 7:
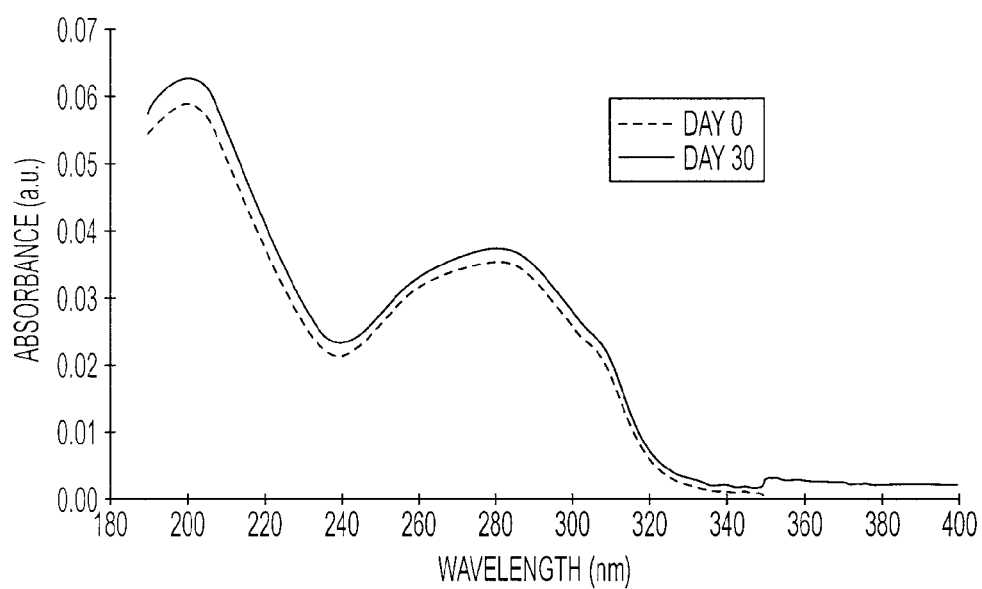
FIG. 7 shows a comparison of the UV spectra on fused silica functionalized with a G4 dendrimer immediately after immobilization (day 0) and 1 month later (day 30).

Because the beads were fabricated in large batches and stored, the stability of the dendrimer on the solid support was corroborated by measuring UV absorbance 30 days after their fabrication. FIGS. 6 and 7 show the results for the G0 and the G4 dendrimers, respectively. The change in the absorbance magnitude likely is due to differences in the blank measurements between both days rather than degradation. The stability was further confirmed by performing hybridization experiments with beads stored for up to 4 months at room temperature with no detrimental effect observed. The same functionalization steps were used to prepare the $SiO_2$ sections for the thermal stability experiments. Although the objective of the current study was to fabricate the selective solid phase using magnetic beads, the thermal stability experiments were performed with $SiO_2$ sections because they present a uniform flat surface for the fluorescence scanning. For the functionalization of the magnetic beads, the most critical new issue in the fabrication was to perform an adequate buffer exchange to avoid agglomeration and to maintain the beads in dispersion during the immobilization of the dendrimer.

An important concern that arises from the functionalization method of the beads is the possibility of bridging neighboring surfaces with a single dendrimer molecule. Given the difference in the feature size between the dendrimers and the magnetic beads, and the fact that dispersion is maintained during the process in a large volume, this effect is assumed to be negligible.

Figure 8A:
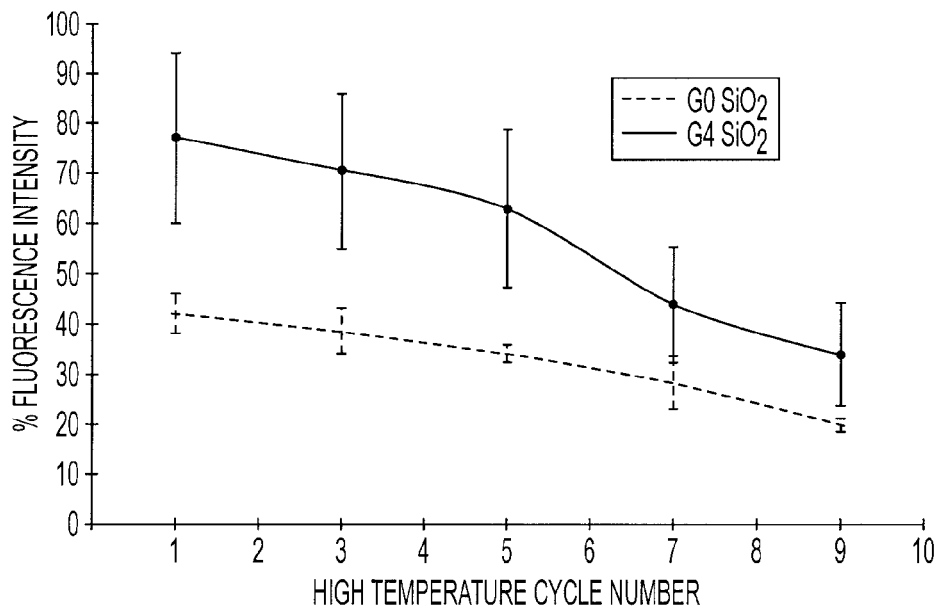
FIG. 8 shows the percentage loss of fluorescence intensity on silicon dioxide sections ($SiO_2$ sections) (A) and magnetic microbeads (B) taken after each hybridization step in five consecutive hybridization-regeneration cycles that correspond to 10 high temperature steps. The $SiO_2$ sections and the magnetic microbeads were functionalized with a G0 or G4 phosphorus dendrimer, and a 25-mer capture probe was then immobilized. The loss in fluorescence was no more than 10% during the first five cycles, demonstrating reasonable stability of the solid phase.

Thermal stability of the selective solid phase—The experiments performed in this part of the study were intended only to demonstrate in a simple manner (by fluorescence) the stability of the solid phase under the conditions required for the single-step selective extraction (high temperature and high salt). FIG. 8(A) shows a plot of the fluorescence intensity versus cycle number for the G0 and G4 $SiO_2$ sections after each hybridization step in five consecutive hybridization-regeneration cycles. A larger loading capacity and hybridization efficiency on the G4 $SiO_2$ sections is clearly shown by the 35% difference in the intensity with respect to the G0 $SiO_2$ section during the first cycle. Although there is a significant intensity reduction by the 10th cycle (50%), the loss is less than 10% during the first five cycles, demonstrating that the solid phase is reasonably stable at high temperature and ionic strength conditions.

Figure 8B:
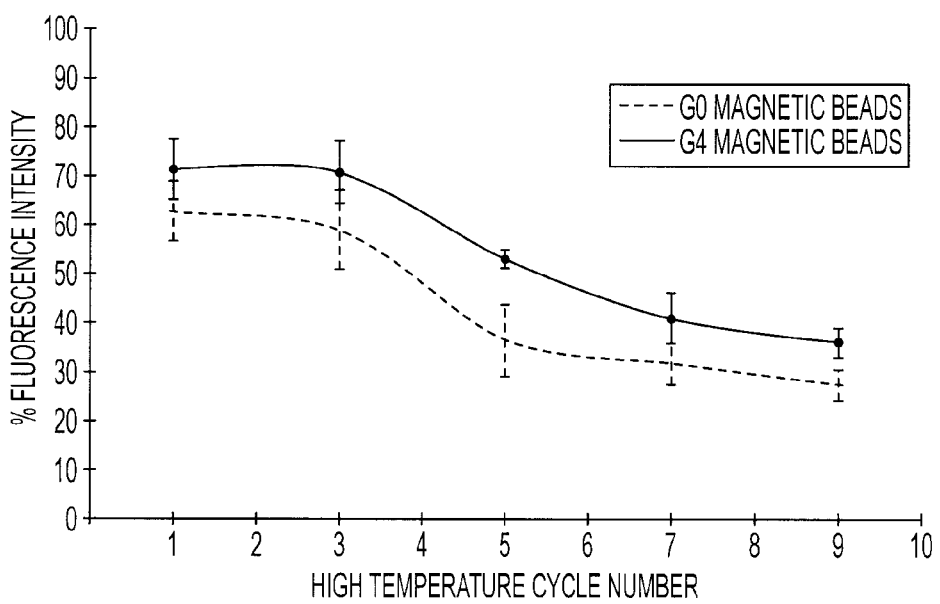

The successful immobilization of the dendrimers on the magnetic beads and the covalent attachment of probe 1 were corroborated by fluorescence imaging after hybridization with target 1. The thermal stability of the immobilized capture probes on the magnetic beads was also tested by fluorescence after each hybridization step in five consecutive regeneration-hybridization cycles. FIG. 8(B) shows a plot of the intensity values for the G0 and G4 beads. In comparison with the $SiO_2$ sections, a larger decrease in intensity is observed at the sixth high temperature cycle. The loss of beads between each hybridization and regeneration cycle contributes partly to this effect. After the sixth regeneration cycle, the intensity of the magnetic beads remained stable while that of the $SiO_2$ sections decreased. The decrease in fluorescence was due to the differences between the bond formed with the $SiO_2$ sections and that formed with the magnetic beads. The reaction of the ethoxy group relies on the Si—O bond that is less stable than the one formed with the pendant OH group of the carbon chain in the PVA shell of the magnetic beads.

FIG. 8(B) also shows that the difference in the loading capacity between the G0 and G4 beads is not as evident as that between the G0 and the G4 $SiO_2$ sections. One reason for this might be that the maximum loading capacity of the G4 magnetic beads was not reached. This was corroborated by increasing the initial amount of capture probe, resulting in a difference of up to 20% in the amount of capture probe immobilized with respect to the G0 beads.

The lack of nonspecific binding was corroborated by performing parallel experiments in which target 1 was substituted by sequence 2 (noncomplementary). No fluorescence was detected in the $SiO_2$ sections or the magnetic beads.

Immobilization of long capture probes on the magnetic bead-based solid phase—Most of the published literature on the immobilization kinetics of DNA on solid supports deals with short single-stranded oligonucleotides. In one of the earliest reports concerned with magnetic beads, Lund et al. ("Assessment of methods for covalent binding of nucleic acids to magnetic beads, Dynabeads™, and the characteristics of the bound nucleic acids in hybridization reactions" *Nucleic Acids Res.*, 16 (1988) 10861-10880) immobilized 500-bp single-stranded DNA fragments to study the hybridization efficiency as related to the coupling chemistry; but the immobilization kinetics was not investigated. Only Zammatteo et al. ("Comparison between microwell and bead supports for the detection of human cytomegalovirus amplicons for sandwich hybridization" *Anal. Biochem.*, 253 (1997) 180-189) investigated some of the factors influencing the immobilization kinetics of double-stranded PCR fragments up to 255 bp. There are no known published data on the covalent immobilization of PCR fragments larger than 300 bp on any type of solid support; therefore, it is difficult to compare them directly with the existing literature. The percentage of the capture probe immobilized on the G0 and G4 beads as a function of length is presented in FIG. 9. Three important observations are derived from these results:

1. Two regimes can be identified: one above and one below the 300-bp length mark.
2. For the first regime (>300 bp), as the length increases, the percentage immobilized increases and the difference between both dendrimers is reduced.
3. In the second regime (<300 bp), as the length decreases, the effect of the dendrimers generation is significantly different and correlates with a higher percentage of immobilized probe for G4.

Figure 9:
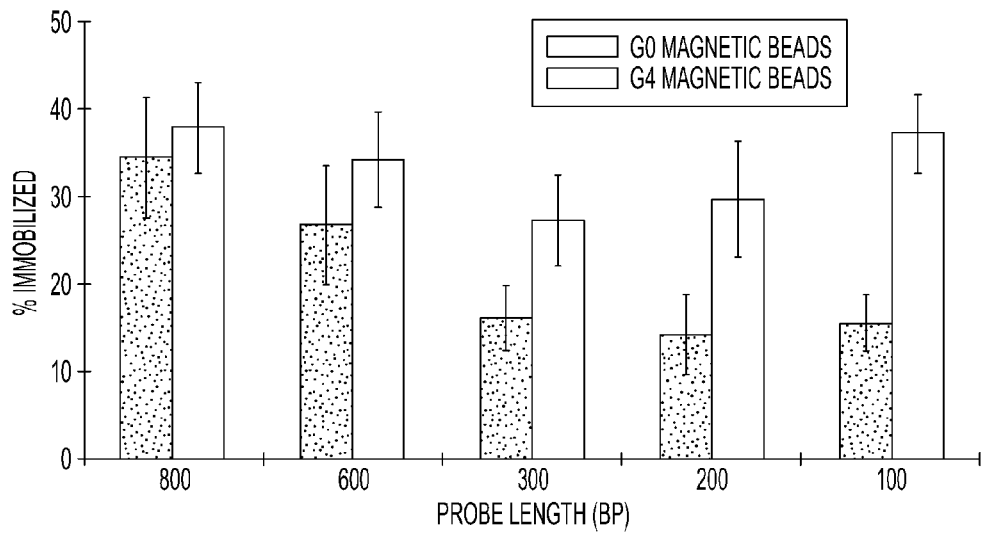
FIG. 9 shows the percentage of capture probe immobilized as a function of the probe length on magnetic beads functionalized with a G0 dendrimer and a G4 dendrimer. Two regimes are identified above and below the 300-bp mark. The immobilization of the larger probes is influenced by long-range electrostatic interactions, as compared with the short ones, where short-range chemical reactions dominate. The data were obtained from 18 independent immobilizations.

To explain the results of FIG. 9, the following assumptions are made:

1. Large DNA fragments exhibit a polymer-like behavior and are present as coiled structures.
2. The larger the probe, the higher its electrical charge.
3. The ionic strength of the buffer remains constant.
4. The initial concentration of the capture probe is the same for all lengths.
5. There is no adsorption of DNA on the surface because the dendrimer is electrically neutral.

In the first regime (>300 bp), there was not a significant difference in the percentage of probe immobilized on G0 or G4 magnetic beads for probes larger than 600 bp. This means that the limiting factor in the immobilization is not the spacing between the surface and the capture probe or the number of reactive sites (number of aldehyde branches). Rather, it is believed that the limiting factor is related to electrostatic repulsion between the coiled DNA fragments anchored at the surface. At this point, the DNA capture probes will not extend into the solution; rather, they will remain in a coiled conformation on the surface of the bead in a manner described by Steel et al. ("Immobilization of nucleic acids at solid surfaces: effect of oligonucleotide length on layer assembly" *Biophys. J.*, 79 (2000) 975-981). The effect of the charge and conformation of double-stranded DNA on the immobilization efficiency has been observed even in fragments as small as 25 bp. If each DNA coil is considered as a unit charge, the electrostatic equilibrium at the surface of the magnetic bead will be reached with the same number of unit charges independent of the number of covalent anchoring sites. Long-range electrostatic repulsion will dominate over the short-range chemical interactions between the amino group of the probe and the aldehyde branches in a similar way as observed by Peterson et al. ("The effect of surface probe density on DNA hybridization" *Nucleic Acids Res.*, 29 (2001) 5163-5168) for thiol-modified oligonucleotides. Although the capture probes have two aminated sides, anchoring at two different sites is possible, but this condition will affect only the topology of the DNA coil rather than the charge profile (Strick et al., "Behavior of supercoiled DNA" *Biophys. J,* 74 (1998) 2016-2028). As the length of the DNA probe decreases to 300 bp, the difference between the percentage of capture probe immobilized on the G0 and G4 beads becomes more evident. Even though the DNA probes are still present as coils, the magnitude of the charge, and thus the electrostatic repulsion between them, has been reduced. The short-range chemical interactions start to become more significant; therefore, the difference in number of available reactive groups (number of aldehyde branches) becomes important. Finally, although the percentage of capture probe immobilized seems to decrease with the probe length, this difference is significant only for the G0 dendrimer, possibly due to steric hindrance between the capture probe and the surface. This is even more evident in the second regime (<300 bp) in which short-range chemical interactions dominate the process. Because the G4 magnetic beads present a surface in which the steric hindrance has been reduced due to a larger spacing, the amino groups of the DNA probes can react easier with the aldehyde branches. The effect of short-range chemical and long-range electrostatic interactions on solid supports has been documented for planar substrates, but these effects are not known to have been investigated on magnetic microbeads.

From FIG. 9, it is also interesting that the final immobilization efficiency of the 100-bp probe is within the range of the 800-bp probe for the G4 beads. Given the strong influence of electrostatic effects on this first regime (>300 bp), the effect of the ionic strength of the buffer plays a more significant role. The larger the DNA probe, the higher the ionic strength required to effectively screen the electrostatic repulsion between the probes. This variable may play a crucial role in the immobilization efficiency of double-stranded DNA. It is believed that the immobilization efficiency of the larger capture probes can be further enhanced by increasing this variable. The only restriction is to maintain a basic pH (>9.0) to allow the reaction of the amino group and the aldehyde to proceed (Peelen et al., "Immobilization of amine-modified oligonucleotides on aldehyde-terminated alkanethiol monolayers on gold" *Langumir,* 21 (2005) 266-271). It is also important to keep in mind that high surface coverage can lead to steric crowding between the probes, and this has a detrimental effect on the hybridization efficiency, even with shorter probes (Zammatteo et al. "Comparison between microwell and bead supports for the detection of human cytomegalovirus amplicons for sandwich hybridization" *Anal. Biochem.,* 253 (1997) 180-189; Zammatteo et al., "Comparison of different strategies of covalent attachment of DNA to glass surfaces to build DNA microarrays" *Anal. Biochem.,* 280 (2000) 143-150; Steel; Peterson). Aside from the variables just discussed, an additional factor that must be taken into account is diffusion. That is, the probe must be accessible over the whole surface area of the bead that requires the beads to be in dispersion. As explained by Zammatteo (*Anal. Biochem.,* 253 (1997) 180-189), the disperse behavior of the beads will reduce these diffusion constraints.

Physical adsorption and shedding capture probe onto the solid phase—In any type of solid support onto which DNA is immobilized, there always is the concern that the capture probes might be adsorbed on the surface or just trapped between the covalently linked probes. Three consecutive washes of the beads were performed after removing the probe supernatant and quantified the unbound remnant. The results indicate that no more than 5% of the total amount of immobilized capture probe was present in these washes and that most of it was recovered on the first wash. Also, the quantification of the supernatants during the denaturing step revealed that most of the DNA recovered was single-stranded, as indicated by a high 260/230 value (ratio of double-stranded DNA to single-stranded DNA present in a sample) as expected, confirming the lack of shedding of adsorbed probes from the surface of the beads. Single-stranded DNA is expected to be recovered from this treatment because the objective is to denature the double-stranded probes and remove any noncovalently bound single strand.

Grafting density of the solid phase—The probe density (number of molecules per unit area) was calculated by considering the beads in dispersion and approximating their arrangement as a cubic closest packed structure with a 30% packing efficiency contained in the lower portion of a 0.5 mL polypropylene tube. The number of beads in a single reaction was obtained considering that only 30% of the volume in the tube was occupied by the beads, and the effective surface area onto which the probes interact was calculated based on a 1-μm bead radius. For the 800-bp capture probe, the immobilization density was calculated as approximately $7 \times 10^8$ molecules/cm$^2$. Other groups have reported immobilization densities on the order of $10^{11}$ to $10^{13}$ molecules/cm$^2$, but these experiments were performed using short DNA sequences (<100 bp) (Dugas et al., "Immobilization of single-stranded DNA fragments to solid surfaces and their repeatable specific hybridization: covalent bonding or adsorption?" *Sens. Actuat. B,* 101 (2004) 112-121; Steel et al., "Immobilization of nucleic acids at solid surfaces: effect of oligonucleotide length on layer assembly" *Biophys. J,* 79 (2000) 975-981; Peterson et al., "The effect of surface probe density on DNA hybridization" *Nucleic Acids Res.,* 29 (2001) 5163-5168). The multiple variables described above and the fact that the probes are larger in size and present as double strands might explain the difference in the immobilization density.

Single-step subtractive hybridization of fragmented human genomic DNA—After successful characterization of the solid phase, subtractive hybridization of fragmented human genomic DNA was performed as a model to demonstrate the use of the selective solid phase. The percentage of DNA extracted as a function of the probe length is presented in Table 1.

TABLE 1

Percentages of fragmented human genomic DNA extracted using the magnetic bead-based selective solid phase as a function of the dendrimer generation and the length of the capture probe

| Probe length (bp) | Generation 0 (%) | Generation 4 (%) |
|---|---|---|
| 800 | 63 ± 6 | 82 ± 5 |
| 600 | 53 ± 6 | 71 ± 9 |

Note. The data were obtained from 15 independent subtractions for each condition and the percentage obtained with respect to a reference sample (no subtraction).

In comparison, with the two-step protocol, only 45% of the fragmented human DNA target was extracted using biotinylated COT probes and streptavidin-coated beads. No significant change was observed in the extraction efficiency after 30 and 45 min of hybridization time using this approach. These results demonstrate an enhancement in the capture efficiency of the single-step protocol performed with the bead-based solid phase (up to 80% extraction) over the two-step protocol using streptavidin-coated beads.

Table 1 shows a clear difference in the subtraction efficiency between the G0 and G4 magnetic beads prepared with long capture probes. As discussed previously, there is not a significant difference in the immobilization of the capture probe, meaning that the enhanced performance of the G4 magnetic beads is due to the difference in spacing between the capture probe and the surface of the bead. It is well known that the longer the spacer, the easier it is to overcome the steric hindrance, leading to better hybridization (Shchepinov et al., "Steric factors influencing hybridization of nucleic acids to oligonucleotide arrays" *Nucleic Acids Res.*, 25 (1997) 1155-1161; Hong et al., "Nanoscale-controlled spacing provides DNA microarrays with the SNP discrimination efficiency in solution phase" *Langmuir*, 21 (2005) 42574261) and the capture of longer targets. In this case, the G4 dendrimer extends the probe five times farther than the G0 dendrimer, allowing the hybridization to proceed in conditions similar to those in solution phase. Because the size range of the captured targets cannot be obtained from the fluorospectrometer measurements, 1.2% TAE agarose gels were used to visualize the DNA fragments recovered from the supernatants after the subtractive hybridization. The results showed that the G4 magnetic beads captured DNA fragments 75000 bp. In contrast, DNA fragments subtracted with the G0 magnetic beads are smaller than 5000 bp. Furthermore, these results indicate that the subtraction process did not remove the internal control (NAC-1) confirming the lack of nonspecific binding of the surface of the beads. The fact that even the G0 magnetic beads are capable of hybridizing to the long DNA targets indicates that the long probes are working as extension arms as described by Zammatteo et al., "Comparison between microwell and bead supports for the detection of human cytoniegalovirus amplicons for sandwich hybridization" *Anal. Biochem.*, 253 (1997) 180-189 and "Comparison of different strategies of covalent attachment of DNA to glass surfaces to build DNA microarrays" *Anal. Biochem.*, 280 (2000) 143-150. There is also a higher probability of nucleation sites between the probe and the target that enhances the duplex formation. In addition, the extension of the probe into solution is enhanced by electrostatic repulsion between the surface and the DNA backbone after the blocking step. Although the effect of $NaBH_4$ as reducing agent is to transform the imine (Schiff base) into a stable amine, as a blocking agent it will transform the available aldehydes into negatively charged alcohol groups that repel the negatively charged backbone of the DNA. The DNA capture probes are then left tethered to the surface by the covalent link, extending them into solution through electrostatic repulsion.

The use of long capture probes to capture long targets poses an additional constraint in the experimental conditions on the range of the effective ionic strength of the hybridization buffer. In the experiments performed in this study, better subtraction efficiencies were obtained when the ratio of the sample volume to the hybridization buffer was less than 0.25. For larger ratios (dilute samples) with the same reaction volumes, the effective ionic strength was reduced, as was the hybridization efficiency. When the whole reaction volume of the digested sample (20 μL) was used for the subtraction, the efficiency of the beads prepared with the longer capture probes (800 bp) was reduced at least 10% with respect to the shorter ones independent of the dendrimer generation. This is expected because the stabilization of the duplex after nucleation with the longest capture probes requires higher ionic strength conditions. Evidently, in those applications where the sample cannot be concentrated, this can be a limitation, but the effect can be ameliorated by reducing the ratio through an increase in the hybridization buffer volume or simply in the NaCl concentration in the stock solution.

The specific and selective capture of human DNA over other nucleic acids present in the same sample was corroborated by fluorescence imaging of the beads after performing a subtractive hybridization using Cy3-labeled fragmented human DNA and by specific PCR on the supernatants after subtraction using the targets spiked with adenovirus serotype 4. The results demonstrated that the proposed solid phase is selective toward a specific target and poses it as a good candidate to perform subtractive hybridization prior to downstream processes in pathogen detection. The lack of capture probe shedding under the conditions required for the subtractive hybridization was also confirmed by quantification of the supernatant after performing a blank subtraction with no target.

To corroborate that the targets were hybridized with the capture probes immobilized onto the magnetic beads, the captured human DNA was released by performing sequential elutions at high temperature under variable ionic strength conditions. The results indicated that only 50-60% of the subtracted targets were recovered under these conditions independent of the capture probes' length or dendrimer generation. Although it is possible that the lower molecular weight fragments of the target DNA may be lost during the concentration, it is more likely that a scenario similar to the one described for the immobilization is taking place. That is, the hybridized capture probe targets complex is present as coiled structures in which shorter targets bound to long capture probes remain embedded within the coil, making their release energetically unfavorable. The difficulty in recovering the bound target might be affected by the media conditions used during the subtraction and release steps. It is known that the structure of DNA is highly sensitive to ion and water concentration to a degree where conformational changes can take place. For instance, change from B to Z form can occur in structures with high G-C content (e.g., human DNA) under high salt media (McConnell et al., "DNA structure: what's in charge?" *J. Mol. Biol.*, 304 (2000) 803-820), and it is considered to be a highly stable conformation (Bancroft et al., "The low-temperature crystal structure of the pure-spermine form of Z-DNA reveals binding of a spermine molecule in the minor groove" *Biochemistry*, 33 (1994) 1073-1086). All of these factors make the selection of the elution conditions a difficult task, requiring a systematic study of such conditions (temperature, ion composition, and concentration) to attain a 100% recovery. To further corroborate that the released material was in fact human genomic DNA, a specific amplification of the GADPH human gene was performed on the eluted DNA. The amplified products were visualized through gel electrophoresis that showed a 300 bp characteristic band comparable to that of the internal control.

Example 7

Selective capture of human genomic DNA in a single step using solid glass beads functionalized with a generation 0 phosphorous dendrimer—Solid glass beads (~1 mm) were functionalized with a generation 0 dendrimer. Cot human DNA with an amino terminal was used as the capture probe. The immobilization was performed at room temperature for 4 hours by placing a single bead at the bottom of a 0.5 ml polypropylene tube and adding ~200 ng of the prepared capture probe. The beads were then blocked for non specific binding and the double stranded capture probes converted into single strands by heat denaturation. The DNA target was prepared by fragmentation of genomic DNA followed by the incorporation of a fluorescent label (Cy3). The capture of the Cy3 double stranded DNA target by one or two glass beads was performed by placing the prepared glass bead solid phase in a 0.5 ml polypropylene tube and adding a solution of the hybridization buffer and the Cy3 double stranded DNA target. The composition of the buffers used and the temperature cycling protocol were as described above. Capture of the DNA target was assessed qualitatively by fluorescence imaging and quantitatively by UV spectroscopy. Each solid glass bead was capable of extracting ~20 ng of target.

Example 8

Selective capture of human and pathogenic DNA using structured silicon selective solid phase as a "all in one" platform—Monocrystalline <100> p type crystalline silicon was used to fabricate structures with different geometries and features sizes. The process comprised a standard photolithographic step followed by dry etching using Reactive Ion Etch (RIE) or Deep Reactive Ion Etch (DRIE) in a fluorine containing plasma to a depth of 2 μm and 50 μm respectively. The resulting structures were then functionalized as described above. Images of the structures are shown in FIG. 10(a-e).

A polydimethylsiloxane (PDMS) gasket with four wells was fabricated and attached to the prepared structured silicon solid phase. Capture probes were immobilized on wells 1, 2 and 3. Wells 1 and 2 were used for selective capture of nucleic acids using capture probes of different lengths. Wells 3 and 4 were used as controls to corroborate lack of probe shedding and of non specific adsorption. Immobilization of the DNA capture probes was carried out by filling each well with 200 μL of capture probe solution and incubating it in a humid environment at 40° C. overnight. Blocking for non specific binding was performed as described above and stripping of the double strand probes was performed by sealing the top of the prepared solid phase with a polymer film and heating the whole device inside a thermal cycler.

After stripping, the film was removed the supernatant discarded and the solid phase rinsed with nuclease free water and dried under a stream of nitrogen. The experiments performed are described in Table 2.

The supernatant recovered from well # 4 was used as a reference (no capture). The lack of signal for the lane corresponding to well # 3 demonstrated lack of shedding of the capture probe. The capture efficiency of the target DNA by these two structures was different as evidenced by the difference in the intensity of lanes 1 and 4 corresponding to well #1 of the structures in FIGS. 10(a-b). This difference in capture efficiency is related to the change in geometry of the solid phase which influences the amount of capture probe immobilized and the steric hindrance. Quantitatively, the percentage of target captured by various solid phases using either a generation 0 or a generation 4 dendrimer is presented in Table 3 which demonstrated the influence of the geometry and the dendrimer generation in the capture efficiency.

TABLE 3

Figure 10A:
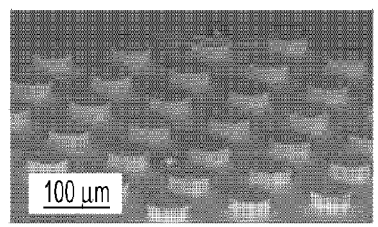
FIG. 10 shows scanning electron microscopy images of the structured silicon solid supports used as selective solid phases. The structures were fabricated through reactive ion etch (RIE) to etch depths of ~2 μm (b, c) or deep reactive ion etch (DRIE) to etch depths of ~50 μm (a, d, e).
Figure 10B:
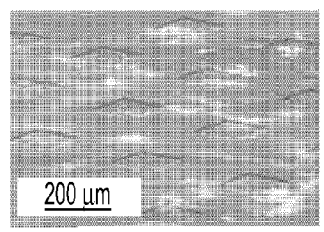
Figure 10C:
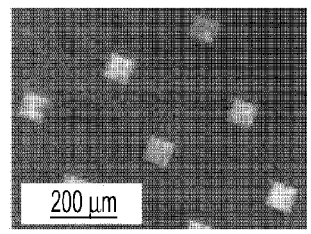
Figure 10D:
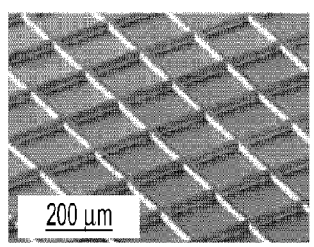
Figure 10E:
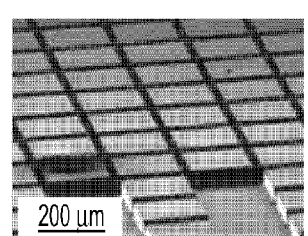

| Structure | G0 | G4 |
|---|---|---|
| FIG. 10(c) | 30% | 40% |
| FIG. 10(b) | 23% | 48% |
| FIG. 10(e) | 15% | 50% |
| FIG. 10(d) | 15% | 55% |

Example 9

Figure 11:
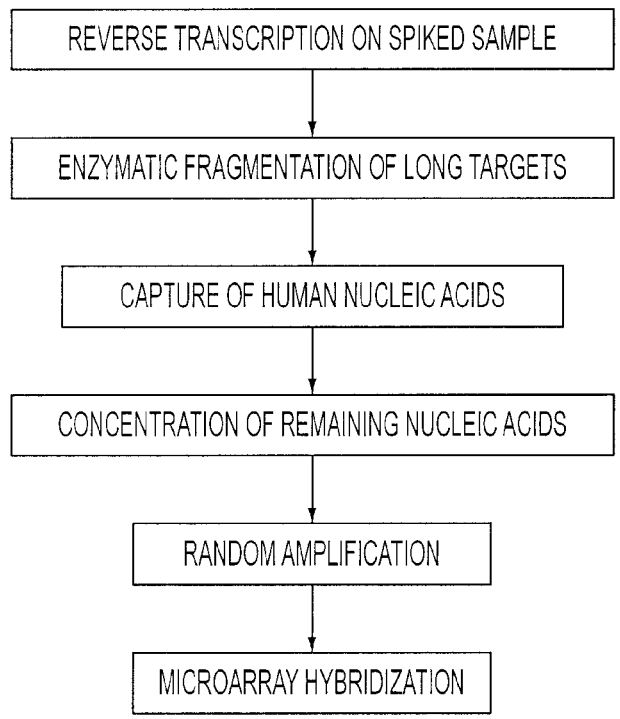
FIG. 11 shows a schematic representation of the protocol used for selective capture of human nucleic acids from complex mixtures and a downstream process to assess the retention of low abundance pathogenic nucleic acids.

Method for selectively capturing nucleic acids from complex mixtures using a thermally stable magnetic bead based solid phase while retaining other sequences of interest present at low abundance—In order to demonstrate the feasibility to capture background (undesired) nucleic acids from a clinical sample, the magnetic bead based solid phase was prepared by immobilizing capture probes designed to subtract human nucleic acids in the presence of small amounts of pathogenic nucleic acids. Influenza A H1N1 RNA and adenovirus serotype 4 DNA were used as model to demonstrate the concept. The protocol used for this purpose is schematically shown in FIG. 11.

The initial sample contained human genomic DNA (hgDNA), human ribosomal RNA (hrRNA), influenza A H1N1 RNA (FluRNA), and adenovirus serotype 4 DNA (Ad4DNA). Since RNA is fragile and prone to degradation at high salt and temperature conditions, the first step in the sample preparation was to convert all the RNA present in the sample (hrRNA and FluRNA) into its equivalent DNA (denoted as hr-cDNA and Flu-cDNA). Since the DNA is unaffected by this step, the product of the reverse transcription

TABLE 2

| | Assay | Target | Post process | Visualization |
|---|---|---|---|---|
| Well #1 | Selective capture of human genomic DNA. | Fragmented human genomic DNA in hybridization buffer | Alcohol precipitation of supernatants | Gel electrophoresis and UV spectroscopy of supernatants |
| Well #2 | Selective capture and subsequent release of pathogenic nucleic acids | cDNA prepared from influenza A H1N1 RNA and DNA extracted from Adenovirus serotype 4 in hybridization buffer | Amplification through the polymerase chain reaction (PCR) of the released targets | Gel electrophoresis |
| Well #3 | Control 1-Lack of DNA capture probe shedding | Hybridization buffer | Alcohol precipitation of supernatants | Gel electrophoresis and UV spectroscopy of supernatants |
| Well #4 | Control 2- Lack of non specific adsorption | Fragmented human genomic DNA in hybridization buffer | Alcohol precipitation of supernatants | Gel electrophoresis and UV spectroscopy of supernatants | step contained hgDNA, hr-cDNA, Ad4DNA, and Flu-cDNA from which the human components (hgDNA, hr-cDNA) represented undesirable background material. The solid phase for the selective capture of these human components must posses capture DNA probes, not only for human DNA, but also for the human ribosomal c-DNA. For this purpose, 3 types of capture probes were prepared: amino-modified Cot human DNA and fragmented human DNA to capture genomic DNA and amino modified 18S and 28S fragments to capture hr-cDNA. The amino labeling for the Cot and human DNA probes was performed with the protocol described above using Sequenase DNA polymerase. The template used for the human DNA probes was prepared by endonuclease digestion of human DNA. The product was amplified through the polymerase chain reaction using random primers and used then as the template for the amino labeling using Sequenase. The capture probes for the hr-cDNA were prepared through the polymerase chain reaction with specific primers.

Each type of capture probe was immobilized independently on a batch of prepared magnetic microbeads. After the blocking and stripping steps the functionalized beads were mixed together and re-aliquoted in 0.5 mL polypropylene tubes each containing 200 μg of solid phase. The capture of the targets was performed as described above with two slight modifications. The first one was an additional pre-hybridization wash of the prepared beads using 50 μL of the hybridization buffer pre-warmed at 70° C. and the second one a larger volume of hybridization buffer (40 μL rather than 30 μL) used for the capture.

The capture of the background nucleic acids was corroborated by gel electrophoresis. The first lane of the gel corresponded to a reference (no capture), and lanes 2, 3, and 4 corresponded to three independent experiments using different amount of beads (185, 125 and 250 μg respectively). The difference in intensity with respect to the reference demonstrated that the targets were being captured and that the amount of beads used was related to the efficiency. The retention of the spiked pathogenic nucleic acids after the capture of background material was corroborated after random amplification and microarray hybridization (RPM v. 1). The presence of characteristic genomic signatures for influenza A H1N1 and adenovirus serotype 4 were identified.

Example 10

Figure 12:
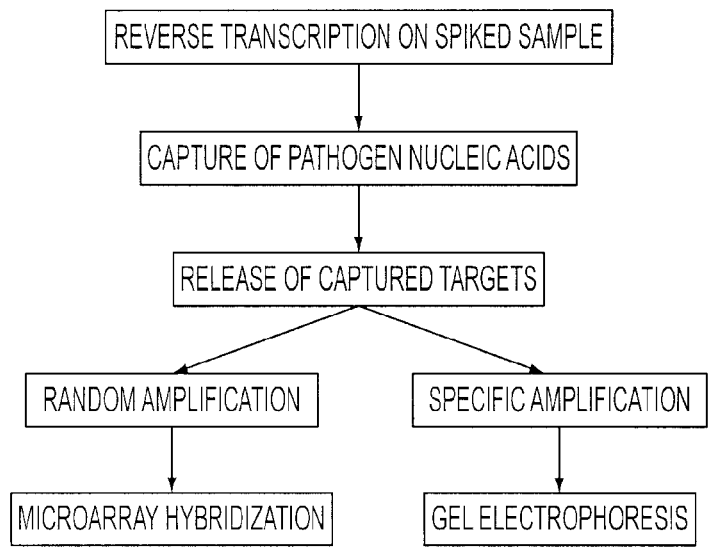
FIG. 12 shows a schematic representation of the protocol used for selective capture of pathogenic nucleic acids from complex mixtures and a downstream process to assess their recovery from the solid phase.

Method for capturing a sequence or sequences of interest present in low abundance in a complex mixture using a thermally stable magnetic bead based solid phase with their subsequent release by heat denaturation—The protocol used for this purpose is schematically shown in FIG. 12. To demonstrate the concept, influenza A H1N1 RNA and adenovirus serotype 4 were used as model of low abundance targets. For this application, the solid phase was prepared with capture probes for these two pathogens. As opposed to the previous example, the background nucleic acids e.g. human genomic DNA and human ribosomal DNA were never retained onto the solid phase but rather, washed away during the post-hybridization wash. The capture probes were synthesized by the polymerase chain reaction (PCR) using primers designed with a 6 carbon spacer. The immobilization of the capture probes was performed in independent bead vials. After the blocking and stripping steps the functionalized beads were mixed together and re-aliquoted in 0.5 mL polypropylene tubes each containing 100 or 200 μg of solid phase. The protocol used for the capture is the same described above. In order to enhance the capture efficiency, an intermediate 70° C. step was added between the denaturation and annealing steps. Prior to the recovery of the captured targets, the beads were washed once with 100 μL of a low salt stripping buffer containing polyoxyethylene sorbitan monolaurate (Tween 20). The solid phase was then resuspended in 20 μL of the same buffer and subject to a first elution by heating to 95° C. for 20 minutes. After the first elution, the supernatant was collected and the solid phase resuspended in 20 μL of nuclease free water pre-warmed at 95° C. A second elution was performed under the same conditions and the supernatants pooled in a final volume of 40 μL. The recovery of the targets was corroborated through the polymerase chain reaction (PCR) using specific primers for these two pathogens. A blank target (only background nucleic acids, no pathogens) was used in one of the samples to corroborate the lack of shedding of capture probes. PCR was also performed on the supernatants collected immediately after the capture to assess the amount of unbound target.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A method comprising:
   providing a solid surface having a dendrimer molecule covalently bound thereto and a single-stranded probe nucleic acid immobilized to the dendrimer;
   wherein the dendrimer is $N_3P_3(O-C_6H_4-X)_6$ or:

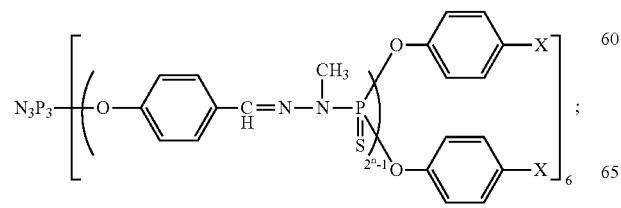

wherein n is a positive integer;
   wherein $N_3P_3$ is hexavalent cyclotriphosphazene;
   wherein the repeating unit in parentheses indicates that phosphorous atom on the right is bound to two repeat units;
   wherein each X is independently selected from —CHO and —CH$_2$—NH—;
   wherein each —CH$_2$—NH— group is directly or indirectly bound to the solid surface or the probe nucleic acid; and
   wherein there is at least one —CH$_2$—NH— group directly or indirectly bound to the solid surface and at least one —CH$_2$—NH— group directly or indirectly bound to the probe nucleic acid;
   contacting the solid surface with a sample suspected or known to contain a double-stranded target nucleic acid;

wherein the solid surface comprises a glass slide, a silicon wafer, a structured silicon wafer, or a plurality of paramagnetic, glass, or silica beads;
wherein a strand of the target nucleic acid is complementary to the probe nucleic acid;
denaturing the target nucleic acids while the sample is in contact with the solid surface at thermal conditions and in a salt concentration sufficient to denature the target nucleic acids to produce denatured nucleic acids;
wherein the-dendrimer molecule remains covalently bound to the solid surface at the thermal conditions and the salt concentration; and
cooling the sample to allow hybridization of the denatured nucleic acids to the probe nucleic acids.

2. The method of claim 1, wherein denaturing is performed at about 90 to about 100° C. in about 3 to about 5 M NaCl.

3. The method of claim 1, wherein the cooling occurs without changing the salt concentration.

4. The method of claim 1, further comprising:
separating the solid surface from the sample containing any remaining nucleic acids that are not hybridized with the probe nucleic acid.

5. The method of claim 4, further comprising:
analyzing the remaining nucleic acids in the sample after the sample is separated from the solid surface to identify an organism.

6. The method of claim 4, further comprising:
performing a polymerase chain reaction on the remaining nucleic acids in the sample after the sample is separated from the solid surface.

7. The method of claim 4, further comprising:
separating the hybridized nucleic acids from the probe nucleic acid by heat denaturation after the sample is separated from the solid surface.

8. The method of claim 4, further comprising:
performing a polymerase chain reaction on the separated nucleic acids.

9. The method of claim 1, wherein the sample contains human nucleic acids and is suspected of containing pathogen nucleic acids.

10. The method of claim 9, wherein the probe nucleic acids are complementary to the human nucleic acids.

11. The method of claim 9, wherein the probe nucleic acids are complementary to the pathogen nucleic acids.

12. An article comprising:
one or more paramagnetic microbeads;
a dendrimer molecule covalently bound to the beads; and
a probe nucleic acid immobilized to the dendrimer;
wherein the dendrimer is $N_3P_3(O\text{---}C_6H_4\text{---}X)_6$ or:

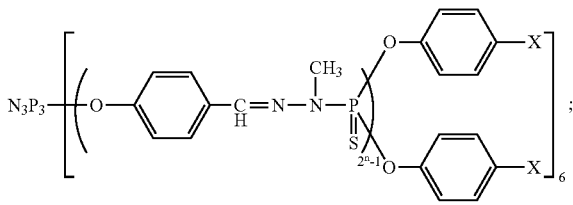

wherein n is a positive integer;
wherein $N_3P_3$ is hexavalent cyclotriphosphazene;
wherein the repeating unit in parentheses indicates that phosphorous atom on the right is bound to two repeat units;
wherein each X is independently selected from —CHO and —$CH_2$—NH—;
wherein each —$CH_2$—NH— group is directly or indirectly bound to the solid surface or the probe nucleic acid; and
wherein there is at least one —$CH_2$—NH— group directly or indirectly bound to the solid surface and at least one —$CH_2$—NH— group directly or indirectly bound to the probe nucleic acid;
wherein the dendrimer molecule remains covalently bound to the microbeads at thermal conditions and a salt concentration suitable for nucleic acid thermal denaturation; and
wherein probe nucleic acids are single-stranded DNA.

13. The article of claim 12, wherein probe nucleic acids are single-stranded human DNA.

14. The article of claim 12, wherein probe nucleic acids are single-stranded pathogen DNA.

15. The method of claim 1, wherein the target nucleic acids are genomic DNA.

16. The article of claim 12, wherein the dendrimer molecule remains covalently bound to the microbeads at thermal conditions and a salt concentration suitable for genomic DNA thermal denaturation.

* * * * *

SEQUENCE LISTING

```
<160> NUMBER OF SEQ ID NOS: 7

<210> SEQ ID NO 1
<211> LENGTH: 25
<212> TYPE: DNA
<213> ORGANISM: E.coli 0157:H7 (EDL933)
<220> FEATURE:
<221> NAME/KEY: modified_base
<222> LOCATION: (1)..(1)
<223> OTHER INFORMATION: aminoadenine

<400> SEQUENCE: 1
nctgcaaata ctaccttggc tcatt                                        25

<210> SEQ ID NO 2
<211> LENGTH: 21
<212> TYPE: DNA
<213> ORGANISM: E.coli 0157:H7 (EDL933)
```

```
<400> SEQUENCE: 2
aatgagccaa ggtagtattt g                                              21

<210> SEQ ID NO 3
<211> LENGTH: 71
<212> TYPE: DNA
<213> ORGANISM: E.coli O157:H7 (EDL933)
<220> FEATURE:
<221> NAME/KEY: modified_base
<222> LOCATION: (71)..(71)
<223> OTHER INFORMATION: Cy3 - fluorescent labeled cytosine

<400> SEQUENCE: 3
aacggttagc aatcgcctga cctgcggcgt catccttcgc gctgttaata cgcaagccag    60
aagacagacg n                                                         71

<210> SEQ ID NO 4
<211> LENGTH: 25
<212> TYPE: DNA
<213> ORGANISM: adenovirus serotype 4

<400> SEQUENCE: 4
gttgctaact acgatccaga tattg                                          25

<210> SEQ ID NO 5
<211> LENGTH: 22
<212> TYPE: DNA
<213> ORGANISM: adenovirus serotype 4

<400> SEQUENCE: 5
cctggtaagt gtctgtcaat cc                                             22

<210> SEQ ID NO 6
<211> LENGTH: 19
<212> TYPE: DNA
<213> ORGANISM: Homo sapiens

<400> SEQUENCE: 6
gtgaaggtcg gagtcacgg                                                 19

<210> SEQ ID NO 7
<211> LENGTH: 21
<212> TYPE: DNA
<213> ORGANISM: Homo sapiens

<400> SEQUENCE: 7
gccagtggac tccacgacgt a                                              21
```